United States Patent
Kai et al.

(10) Patent No.: US 8,221,969 B2
(45) Date of Patent: Jul. 17, 2012

(54) METHOD OF PRODUCING VIRUS

(75) Inventors: Hikaru Kai, Niigata (JP); Masayuki Tsubaki, Niigata (JP); Masato Kurokawa, Kyoto (JP)

(73) Assignees: Sanyo Chemical Industries, Ltd., Kyoto (JP); Denka Seiken Co. Ltd., Tokyo (JP)

( * ) Notice: Subject to any disclaimer, the term of this patent is extended or adjusted under 35 U.S.C. 154(b) by 953 days.

(21) Appl. No.: 10/587,431

(22) PCT Filed: Apr. 19, 2005

(86) PCT No.: PCT/JP2005/007459
§ 371 (c)(1),
(2), (4) Date: Jul. 27, 2006

(87) PCT Pub. No.: WO2005/103235
PCT Pub. Date: Nov. 3, 2005

(65) Prior Publication Data
US 2008/0233148 A1 Sep. 25, 2008

(30) Foreign Application Priority Data
Apr. 19, 2004 (JP) .................................. 2004-122898

(51) Int. Cl.
*C12Q 1/70* (2006.01)
*C07K 5/00* (2006.01)
(52) U.S. Cl. ........................... 435/5; 530/300; 424/204.1
(58) Field of Classification Search ........................ None
See application file for complete search history.

(56) References Cited

U.S. PATENT DOCUMENTS

| | | | |
|---|---|---|---|
| 5,618,531 A * | 4/1997 | Cherksey | 424/93.7 |
| 6,184,348 B1 * | 2/2001 | Ferrari et al. | 530/350 |
| 6,214,618 B1 * | 4/2001 | Hillegas et al. | 435/396 |
| 6,372,223 B1 * | 4/2002 | Kistner et al. | 424/209.1 |
| 2003/0108860 A1 * | 6/2003 | Reiter et al. | 435/5 |
| 2006/0148074 A1 | 7/2006 | Gorfien et al. | |
| 2006/0183224 A1 | 8/2006 | Aerts et al. | |

FOREIGN PATENT DOCUMENTS

| | | |
|---|---|---|
| JP | 2000-517188 | 12/2000 |
| JP | 2003-189848 | 7/2003 |
| JP | 2003-210166 | 7/2003 |
| JP | 2003-304868 A | 10/2003 |
| JP | 2004-000471 | 1/2004 |
| WO | WO-95/01998 | 1/1995 |
| WO | WO-96/15231 | 5/1996 |
| WO | WO-9808934 | 3/1998 |
| WO | WO-2004005493 | 1/2004 |
| WO | WO 2004/078955 A1 * | 9/2004 |
| WO | WO-2004078955 | 9/2004 |

OTHER PUBLICATIONS

Monath et al., ACAM2000 clonal Vero cell culture vaccinia virus (New York City Board of Health strain)—a second-generation smallpox vaccine for biological defense, 2004, International Journal of Infectious Diseases, vol. 852, pp. S31-S44.*
Koff, Review article: vaccination and viral hepatitis—current status and future prospects, 2007, Alimentary Pharmacology and Therapeutics, vol. 26, pp. 1285-1292.*
Rupp and Bernstein, The potential impact of a prophylactic herpes simplex vaccine, 2008, Expert Opinion of Emerging Drugs, vol. 13, No. 1, pp. 41-52.*
Halpin and Mungall, Recent progress in henipavirus research, 2007, Comparative Immunology, Microbiology and Infectious Diseases, vol. 30, pp. 287-307.*
Wang and Ouyang, Recycle of Cytodex-3 in Vero cell culture, 1999, Bioprocess Engineering, vol. 21, pp. 207-210.*
Kistner et al., Development of a Vero Cell-Derived Influenza Whole Virus Vaccine, 1999, Developments in Biological Standardization, vol. 98, pp. 101-110.*
Kobatake et al., Design of a thermostable cell adhesion protein, 1999, Biotechnology Techniques, vol. 13, pp. 23-27.*
Sanderson and Smith, Vaccinia Virus Induces Ca2+-Independent Cell-Matrix Adhesion during the Motile Phase of Infection, 1998, Journal of Virology, vol. 72, No. 12, pp. 9924-9933.*
Otfried Kistner et al., "Development of a Novel Mammalian Cell (Vero) Derived Influenza Vaccine" Poster Presented at: Options for Control of Influenza V, Japan, Oct. 7-11, 2003.
International Search Report (PCT/JP2005/007459) dated Jul. 26, 2005.
Murakami et al., "Introduction to Cell Engineering," *Corona Publishing Co., Ltd.*, p. 68 (1994).
The Japanese Tissue Culture Association, Tissue Culture Technique (Basics), *Asakura Publishing Co., Ltd.*, 1 page (1999).

* cited by examiner

*Primary Examiner* — Agnieszka Boesen
(74) *Attorney, Agent, or Firm* — McDermott Will & Emery LLP

(57) ABSTRACT

It is intended to provide a safe and efficient method of producing a virus which is free from animal-origin components in the whole process from culturing adhesive cells to producing the virus on an industrial scale by the cell culture. Namely, a method of producing a virus comprising: adhering adhesive cells to a support which has a polypeptide (P) having at least one cell-adhesive minimum amino acid sequence (X) per molecule, and is free from animal-origin components; culturing the adhesive cells in a medium free from animal-origin components; subculturing the cultured adhesive cells using a cell dispersing agent: free from animal-origin components; and then inoculating and proliferating a virus in the cells obtained by culturing the adhesive cells.

6 Claims, 3 Drawing Sheets

METHOD OF PRODUCING VIRUS

SEQUENCE LISTING

The instant application contains a Sequence Listing which has been submitted in ASCII format via EFS-Web and is hereby incorporated by reference in its entirety. Said ASCII copy, created on Mar. 30, 2011, is named 86039015.txt and is 121,326 bytes in size.

TECHNICAL FIELD

The present invention relates to a method of producing a virus.

BACKGROUND ART

Recently, a risk of zoonotic infectious disease such as BSE (Bovine Spongiform Encephalopathy) infection and Avian Influenza virus infection, has started to be a concern. Moreover, products using ingredients or materials primarily originated from animals (such as vaccines, blood preparations, cell culture/genetic recombinant preparations, and cellular tissue medical products) have problems of a high risk where an infectious agent is mixed thereinto, and an undeniable likelihood of containing an unknown infectious agent, as well as a limitation in the inactivation treatment of infectious agents, and the like. As a countermeasure against such problems, legal countermeasures for safety have been enhanced, such as newly providing a framework for "bio-originated products" by the amendment of Japanese Pharmaceutical Law in 2003, and there has become a desire for the development of medical products free from animal-origin components.

Many attempts have been made for obtaining a culture condition not requiring a serum, such as bringing serum-free mediums free from animal-origin components into the market by respective medium manufacturers. However, in a culture method using a serum-free medium and a microcarrier where the surface of the carrier is electrically charged at an appropriate amount so as to adhere cells, as a support for culturing adhesive cells, there has been a problem in that the attachment rate to the microcarrier is reduced, making it difficult to efficiently culture a large amount of cells. As a result, conventionally, under such a culture condition, there has been used a carrier containing animal-origin components such as a microcarrier coated with denatured pig collagen, as described for example in Non Patent Document 1.

Moreover, there is disclosed in Patent Document 1, a bead for culturing animal cells which has a high cell-adhering property and a high cell-proliferating property, and, even in a serum-free culture medium, gives a cell-adhering property and a cell-proliferating property which are equivalent or more to those in serum-containing medium. However, although Patent Document 1 shows that cells can be efficiently cultured under a serum-free condition in a cell culture, there is no disclosure of a condition for producing a virus such as a virus inoculation or proliferation method.

Moreover, there is disclosed in Patent Document 2, a method of producing a virus including steps of: obtaining a vertebrate cell culture such as Vero cells; proliferating the cells only in a protein-free medium (free from serum or non-serum protein); infecting this culture with a virus; incubating the virus-infected cell culture; proliferating the virus in the medium; and producing the virus-containing medium. Furthermore, there is disclosed a usage of a protease originated from a procaryote supply source as a substance which enhances the virus activity. Patent Document 2 describes that, according to this method, the obtained virus do not contain various impurity compounds originated from a human or animal supply source, nor a protein serving as a pathogenic substance. However, in an Example a trypsin which is an animal-origin component is used as a substance which enhances the virus activity.

Furthermore, there is disclosed in Patent Document 3, a method of producing a virus infected insect cell not using a naturally-originated protein but using a cell-adhesive support having a high cell-adhering property. This production method is a method of producing a virus infected insect cell, comprising steps of using a cell-adhesive artificial peptide and/or a cell-adhesive auxiliary artificial peptide to adhere a poikilothermic animal-origin cell and a substrate, and using this cell-adhered substrate for culturing cells. Patent Document 3 describes that, by not using a naturally-originated protein for a substrate, there is no risk of containing an infectious substance such as a human-infective virus, and the safety is high. However, there is no disclosure of a cell dispersing agent free from animal-origin components or an adhesive cell originated from a homoiothermic animal. On the other hand, for the subculture of cells in Non Patent Document 1, an animal-origin protease (such as pig-origin trypsin) is used as a cell dispersing agent.

Patent Document 1: Japanese Unexamined Patent Publication No. 2003-189848
Patent Document 2: Japanese Patent Publication No. 3158157 (WO96115231 pamphlet)
Patent Document 3: Japanese Unexamined Patent Publication No. 2003-210166
Non Patent Document 1: Otfried Kistner et al. "Development of a Novel Mammalian Cell (Vero) Derived influenza Vaccine" Poster Presented at: Options for Control Of Influenza V, Okinawa, Japan, Oct. 7-11, 2003

DISCLOSURE OF THE INVENTION

Problems to be Solved by the Invention

Therefore, an object of the present invention is to provide a safe and efficient method of producing a virus which is free from animal-origin components in the whole process from culturing adhesive cells to producing the virus on an industrial scale by the cell culture.

Means for Solving the Problem

The above problems have been considered and earnestly studied, resulting in a finding of a safe and efficient method of producing a virus by using a culture material which is free from animal-origin components, and thus conceiving the present invention.

The scope of the method of producing a virus of the present invention comprises the points of: adhering adhesive cells to a support which has a polypeptide (P) having at least one cell-adhesive minimum amino acid sequence (X) per molecule, and is free from animal-origin components; culturing the adhesive cells in a medium free from animal-origin components; subculturing the cultured adhesive cells using a cell dispersing agent free from animal-origin components; and then inoculating and proliferating a virus in the cells obtained by culturing the adhesive cells.

Effects of the Invention

In the method of producing a virus of the present invention, the virus can be safely and efficiently produced. Therefore, the method of the present invention is suitable for producing a vaccine.

BEST MODE FOR CARRYING OUT THE INVENTION

Figure 1:
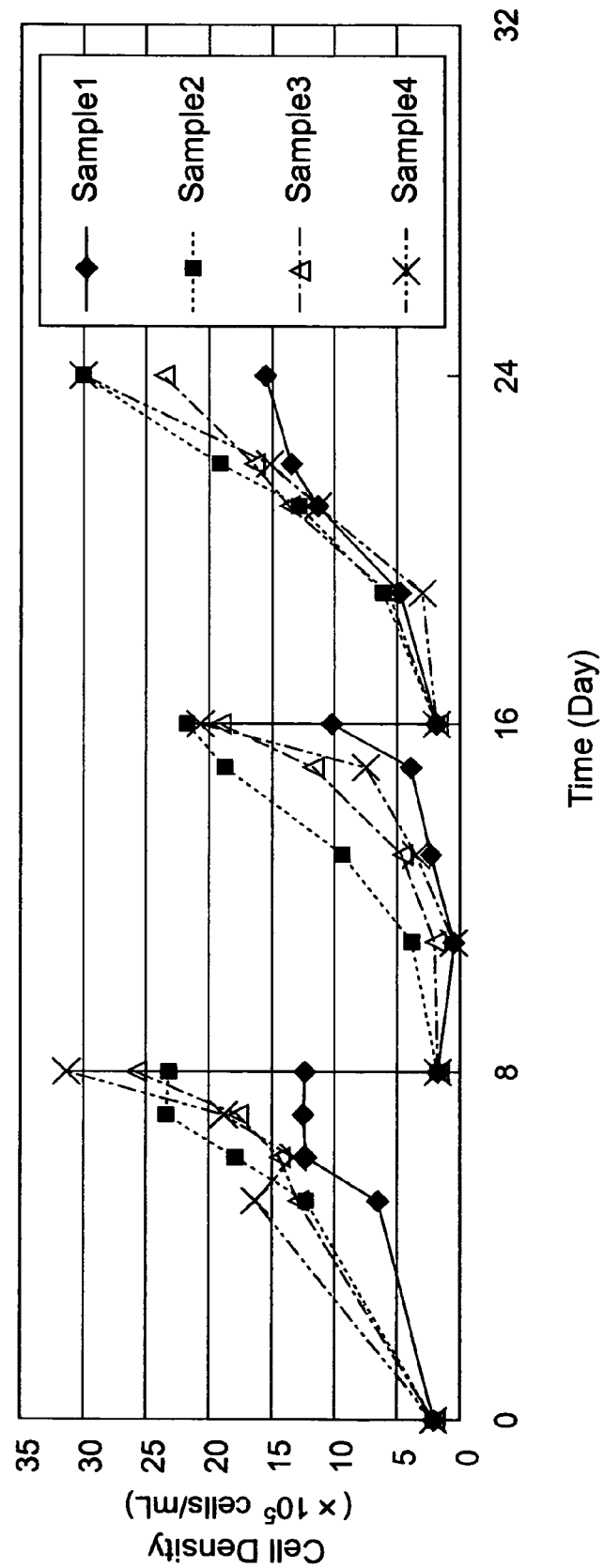
FIG. 1 is a graph showing changes in cell density with time in Example 1 and Comparative Examples 1 to 3.

In the present invention, "free from animal-origin components" means free from components originated from homoiothermic animals, in particular, animals such as mammals (for example, human, cattle, pig, dog, rabbit, cat, and the like), birds, and fishes.

Moreover, in the present invention, an adhesive cell is not specifically limited as long as it is a homoiothermic animal-origin cell which grows by adhering onto a solid surface and is capable of proliferating a virus. Examples thereof include an epithelial cell (such as Vero, MDCK, CHO, HEK293, and COS), a tumor cell (such as Hela and VACO), an endothelial cell (such as HUVEC and DBAE), a leukocyte (such as HIT-T15), a fibroblast (such as WI38, BHK21, and SFME), a muscle cell (such as HL1 and C2C12), a nerve/endocrine cell (such as ROC-1 and 1MR-32), and a primary cell (such as primary chick embryo, primary quail embryo, and primary rabbit kidney). Among these, preferred are an epithelial cell and a primary cell, more preferably Vero, MDCK, and a primary cell, particularly preferably Vero and MDCK, and most preferably Vero.

Moreover, examples of the virus to be inoculated in the adhesive cells in the present invention include Flaviviridae (such as a Yellow fever virus, a Japanese encephalitis virus, a hepatitis C virus, and a Dengue fever virus), Orthomyxoviridae (such as an Influenza virus), Adenoviridae (such as a Human adenovirus 1-34), Herpesviridae (such as a Herpes simplex I, a Herpes simplex II, a Pseudorabies virus, a Varicella-zoster virus, and a Human cytomegalovirus), Picornaviridae (such as an Aphthovirus O, a Foot-and-mouth disease virus, a Poliovirus, and a Hepatitis A virus), Paramyxoviridae (such as a Measles virus, a Mumps virus, and a Sendai virus), Togaviridae (such as a Rubella virus and an Encephalitis virus), Poxyiridae (such as a Vaccinia virus, a Variola virus, a Cowpox virus, and a Monkeypox virus), Retroviridae (such as a Human immunodeficiency virus (HIV) and a Human T-lymphotropic virus), and Coronaviridae (such as an Avian infections bronchitis virus) (Dictionary of biochemistry (second edition), published by Tokyo Kagaku Dojin (11 Sep. 1997<<. Among these, preferred are viruses belonging to Flaviviridae, Orthomyxoviridae, Adenoviridae, Herpesviridae, Picornaviridae, Paramyxoviridae, Togaviridae, or Poxyiridae, more preferred are viruses belonging to Flaviviridae, Orthomyxoviridae, Paramyxoviridae, or Togaviridae, particularly preferred are viruses belonging to Orthomyxoviridae, Paramyxoviridae, or Togaviridae, and most preferred are viruses belonging to Orthomyxoviridae.

Furthermore, the culture material (such as a medium, a cell dispersing agent, and a support for adhering adhesive cells) free from animal-origin components used in the present invention is free from animal-origin components, and therefore has advantages in that: it can minimizes a likelihood of contamination due to foreign substances; it is free from unknown infectious agents; and it has a low risk of being mixed with infectious agents, and thus there is no need for performing a treatment for deactivating the infectious agents. Hereunder is a detailed description of the culture material free from animal-origin components.

The medium used for culturing an adhesive cell or producing a virus is not specifically limited as long as it is a medium free from a serum or a protein being animal-origin components (hereunder, serum-free medium). Examples thereof include a commercially available serum-free medium {such as OPTIPRO™SFM medium (manufactured by Invitrogen), VP-SFM (manufactured by Invitrogen), and EX-CELL 525 (manufactured by JRH Bioscience)}, a basal medium (such as Eagle MEM medium, Dulbecco's Modified Eagle medium, Iscove's medium, RPMI1640 medium, Ham F10 medium, Ham F12 medium, MCDB 105 medium, MCDB 107 medium, MCDB 110 medium, MCDB 131 medium, MCDB 151 medium, MCDB 152 medium, MCDB 153 medium, MCDB 201 medium, MCDB 302 medium, and MEDIUM 199) and the mixed medium thereof. Among these, from the viewpoints of medium preparation etc., preferred is a commercially available serum-free medium, more preferred are OPTIPRO™SFM medium, VP-SFM, and EX-CELL 525, particularly preferred are VP-SFM and EX-CELL 525, and yet more particularly preferred are VP-SFM. This VP-SFM is suitable for culturing a cell system, such as Vero, COS-7, MDCK, BHK-21, and HEP-2, that is used for proliferation of a virus. The serum-free medium may be appropriately added with, as a non animal-origin additive, a hormone (such as insulin and hydrocortisone) originated from genetic recombinant bacteria or the like, a cell growth factor (such as an epidermal growth factor (EGF), a platelet-derived growth factor (PDGF), and a fibroblast growth factor (FGF)), and an antimicrobial (such as kanamycin), so as to stably improve the cell-proliferating property.

The material of the support is not specifically limited as long as it is a material capable of adhering an adhesive cell. However, from the viewpoints of cytotoxicity etc., it preferably has the following materials as a primary component.

(1) Synthetic polymer: vinyl resin, polyester, polyurethane, epoxy resin, nylon, polycarbonate, and the like.
(2) Natural polymer: cellulose, cellulose derivative (such as cellulose diacetate and cellulose triacetate), dextran, and the like.
(3) Inorganic substance: aluminum oxide, hydroxyapatite, titanium oxide, silica, glass, and the like.

Among these, preferred are a synthetic polymer, a natural polymer, and hydroxyapatite, more preferred are a synthetic polymer and a natural polymer, particularly preferred is a synthetic polymer, and most preferred are a vinyl resin and nylon.

Examples of the vinyl resin include a vinyl monomer (such as an acrylic monomer, alkene, and styrene), and a polymer comprising polyfunctional monomers and the like as a constitutional unit as necessary (such as polystyrene, crosslinked polystyrene, polymethyl(metha)acrylate, poly(metha)acrylamide, crosslinked polyacrylamide (such as a copolymer of acrylamide and ethylene glycol diacrylate), and poly(metha)

acrylonitrile). Among these, preferred is a resin comprising styrene as an essential constitutional unit, and more preferred is crosslinked polystyrene.

Examples of the polyfunctional monomer include divinylbenzene, ethylene glycol di(metha)acrylate, trivinylbenzene, and trimethylolpropane tri(metha)acrylate.

The shape of the support is not specifically limited as long as it is a shape capable of adhering an adhesive cell, and may be anyone of a plate, a Petri dish, a T-flask, a roller bottle, a microcarrier, a hollow fiber, a sheet (such as a film, a foam (sponge), and a cloth), and a gel. Among these, from the viewpoints of the culture volume etc., preferred are a Petri dish, a T-flask, a roller bottle, a microcarrier, and a hollow fiber, more preferred are a roller bottle, a microcarrier, and a hollow fiber, particularly preferred are a microcarrier and a hollow fiber, and most preferred is a microcarrier.

The form of the microcarrier includes a solid type and a porous type, anyone of which may be used. However, a solid type is preferred, from the viewpoints of the efficiency of supplying nutrients and oxygen to the cells, the recovery rate of the cells, etc. Moreover, as to the shape of the microcarrier, either globular or flat (oval) may be used:

In the case of the solid type, the particle diameter (μm) of the microcarrier is preferably 20 to 2000, more preferably 40 to 1000, and particularly preferably 80 to 500. On the other hand, in the case of the porous type, the particle diameter (μm) is preferably 30 to 25000, more preferably 60 to 12000, and particularly preferably 120 to 6000. Within this range, the cell growth is further increased.

The true specific gravity of the microcarrier is not specifically limited. However, in a general method of culturing while stirring a microcarrier together with a medium, preferably beads are floating during the stirring, and they are sedimented when the stirring is stopped. From such a viewpoint, the true specific gravity (g/cm3) of the microcarrier is preferably 1.00 to 1.10, more preferably 1.01 to 1.08, and particularly preferably 1.01 to 1.05.

The microcarrier can be readily commercially available, and the products as follows maybe used.

(1) Made from polystyrene: Biosilon (manufactured by Nalge Nunc International), Plastic beads (manufactured by Solohill Engineering), Cytosphere (manufactured by Lux), and the like.
(2) Made from polyacrylamide: Biocarrier (manufactured by Bio-Rad Laboratories), and the like.
(3) Made from polyurethane: PUF (manufactured by INOAC), and the like.
(4) Made from cellulose: Cellsnow (manufactured by Biomaterial), and the like.
(5) Made from dextran: Cytodex (manufactured by Amersham Pharmacia), and the like.
(6) Made from glass: SIRAN (manufactured by Scott Medical Products), and the like.

The support contains a polypeptide (P) having at least one cell-adhesive minimum amino acid sequence (X) per molecule. By containing the polypeptide (P), a highly efficient production of a virus can be realized without using an animal-origin material.

The "cell-adhesive minimum amino acid sequence" means a minimum amino acid sequence having a property of being recognized by an integrin receptor of a cell, and thus facilitating adhering of the cell to a substrate.

From the viewpoints of cell-adhering property etc., the number of cell-adhesive minimum amino acid sequences (X) contained in the polypeptide (P) is preferably 1 to 50 per molecule (P), more preferably 3 to 30, and particularly preferably 4 to 20.

As for the cell-adhesive minimum amino acid sequence (X), any sequence may be used as long as it acts as an adhesive signal, and there may be used those described in "Pathophysiology" Vol. 9, No. 7, 1990, p527, published by Nagai Shoten Co., Ltd. Among these, from the viewpoints of abundant types of cells that are readily adhered, etc., preferred are an Arg Gly Asp (SEQ ID NO: 70) sequence, a Leu Asp Val (SEQ ID NO: 73) sequence, a Leu Arg Glu sequence, a His Ala Val (SEQ ID NO: 72) sequence and sequences represented by SEQ ID NOs:1 to 8, more preferred are an Arg Gly Asp (SEQ ID NO: 70) sequence, a His Ala Val (SEQ ID NO: 72) sequence, and a sequence represented by SEQ ID NO:7, and particularly preferred are an Arg Gly Asp (SEQ ID NO: 70) sequence.

From the viewpoints of improving the thermal stability of (P) etc., the polypeptide (P) preferably has an auxiliary amino acid sequence (Y) in addition to the cell-adhesive minimum amino acid sequence (X).

As for the auxiliary amino acid sequence (Y), there may be used an amino acid sequence other than the minimum amino acid sequence (X). From the viewpoints of improving the thermal resistance of the polypeptide (P) etc., it is preferably a sequence having Gly and/or Ala.

Examples of the auxiliary amino acid sequence (Y) include sequences having a (Gly Ala)a (SEQ ID NO: 55) sequence, a (Gly Ala Gly Ala Gly Ser)b (SEQ ID NO: 56) sequence, a (Gly Ala Gly Ala Gly Tyr)c (SEQ ID NO: 57) sequence, a (Gly Ala Gly Val Gly Tyr)d (SEQ ID NO: 58) sequence, a (Gly Ala Gly Tyr Gly Val)e (SEQ ID NO: 59) sequence, an (Asp Gly Gly (Ala)f Gly Gly Ala)g (SEQ ID NO: 60) sequence, a (Gly Val Pro Gly Val)h (SEQ ID NO: 61) sequence, a (Gly)i (SEQ ID NO: 62) sequence, an (Ala)j (SEQ ID NO: 63) sequence, a (Gly Gly Ala)k (SEQ ID NO: 64) sequence, a (Gly Val Gly Val Pro)m (SEQ ID NO: 65) sequence, a (Gly Pro Pro)n (SEQ ID NO: 66) sequence, a (Gly Ala Gln Gly Pro Ala Gly Pro Gly)o (SEQ ID NO: 67) sequence, a (Gly Ala Pro Gly Ala Pro Gly Ser Gln Gly Ala Pro Gly Leu Gln)p (SEQ ID NO: 68) sequence, and/or a (Gly Ala Pro Gly Thr Pro Gly Pro Gln Gly Leu Pro Gly Ser Pro)q (SEQ ID NO: 69) sequence. Among these, preferred are sequences having a (Gly Ala)a (SEQ ID NO: 55) sequence, a (Gly Ala Gly Ala Gly Ser)b (SEQ ID NO: 56) sequence, a (Gly Ala Gly Ala Gly Tyr)c (SEQ ID NO: 57) sequence, a (Gly Ala Gly Val Gly Tyr)d (SEQ ID NO: 58) sequence, a (Gly Ala Gly Tyr Gly Val)e (SEQ ID NO: 59) sequence, a (Asp Gly Gly (Ala)f Gly Gly Ala)g (SEQ ID NO: 60) sequence, a (Gly Val Pro Gly Val)h (SEQ ID NO: 61) sequence, a (Gly Val Gly Val Pro)m (SEQ ID NO: 65) sequence, and/or a (Gly Pro Pro)n (SEQ ID NO: 66) sequence, more preferred are sequences having a (Gly Ala Gly Ala Gly Ser)b (SEQ ID NO: 56) sequence, a (Gly Val Pro Gly Val)h (SEQ ID NO: 61) sequence, a (Gly Val Gly Val Pro)m (SEQ ID NO: 65) sequence, and/or a (Gly Pro Pro)n (SEQ ID NO: 66) sequence, and particularly preferred are sequences having a (Gly Ala Gly Ala Gly Ser)b (SEQ ID NO: 56) sequence.

Here, a is an integer of 5 to 100, b, c, d and e are integers of 2 to 33, f is an integer of 1 to 194, g is an integer of {I} to {200/(6+f)} that has been truncated to omit fractions, h is an integer of 2 to 40, i and j are integers of 10 to 200, k is an integer of 3 to 66, m is an integer of 2 to 40, n is an integer of 3 to 66, 0 is an integer of 1 to 22, and p and q are integers of 1 to 13. The auxiliary amino acid sequence (Y) preferably contains glycine (Gly) and/or alanine (Ala). If glycine (Gly) and alanine (Ala) are contained, the proportion of total content thereof (%) is preferably 10 to 100 based on the total number of amino acids of the auxiliary amino acid sequence (Y), more preferably 20 to 95, particularly preferably 30 to 90, and most preferably 40 to 85. Within this range, the thermal resistance is further improved.

If both of glycine (Gly) and alanine (Ala) are contained, their content number ratio (Gly/Ala) is preferably 0.03 to 40, more preferably 0.08 to 13, and particularly preferably 0.2 to 5. Within this range, the thermal resistance is further improved.

From the viewpoints of improving the thermal resistance etc., the number of the auxiliary amino acid sequences (Y) contained in the polypeptide (P) is preferably 2 to 51 per molecule (P), more preferably 3 to 35, and particularly preferably 4 to 20. Moreover, the polypeptide (P) may contain a plurality of types of auxiliary amino acid sequences (Y).

The auxiliary amino acid sequence having a (Gly Ala)a (SEQ ID NO: 55) sequence includes amino acid sequences represented by SEQ ID NOs: 9 to 11.

The auxiliary amino acid sequence having a (Gly Ala Gly Ala Gly Ser)b (SEQ ID NO: 56) sequence includes amino acid sequences represented by SEQ ID NOs: 12 to 14.

The auxiliary amino acid sequence having a (Gly Ala Gly Ala Gly Tyr)c (SEQ ID NO: 57) sequence includes amino acid sequences represented by SEQ ID NOs: 15 to 17.

The auxiliary amino acid sequence having a (Gly Ala Gly Val Gly Tyr)d (SEQ ID NO: 58) sequence includes amino acid sequences represented by SEQ ID NOs: 18 to 20.

The auxiliary amino acid sequence having a (Gly Ala Gly Tyr Gly Val)e (SEQ ID NO: 59) sequence includes amino acid sequences represented by SEQ ID NOs: 21 to 23.

The auxiliary amino acid sequence having an (Asp Gly Gly (Ala)f Gly Gly Ala)g (SEQ ID NO: 60) sequence includes amino acid sequences represented by SEQ ID NOs: 24 to 26.

The auxiliary amino acid sequence having a (Gly Val Pro Gly Val)h (SEQ ID NO: 61) sequence includes amino acid sequences represented by SEQ ID NOs: 27 to 30.

The auxiliary amino acid sequence having a (Gly)i (SEQ ID NO: 62) sequence includes amino acid sequences represented by SEQ ID NOs: 31 to 33.

The auxiliary amino acid sequence having an (Ala)j (SEQ ID NO: 63) sequence includes amino acid sequences represented by SEQ ID NOs: 34 to 36.

The auxiliary amino acid sequence having a (Gly Gly Ala)k (SEQ ID NO: 64) sequence includes amino acid sequences represented by SEQ ID NOs: 37 to 39.

The auxiliary amino acid sequence having a (Gly Val Gly Val Pro)m (SEQ ID NO: 65) sequence includes amino acid sequences represented by SEQ ID NOs: 40 to 42.

The auxiliary amino acid sequence having a (Gly Pro Pro)n (SEQ ID NO: 66) sequence includes amino acid sequences represented by SEQ ID NOs: 43 to 45.

The auxiliary amino acid sequence having a (Gly Ala Gln Gly Pro Ala Gly Pro Gly)o (SEQ ID NO: 67) sequence includes amino acid sequences represented by SEQ ID NOs: 46 to 48.

The auxiliary amino acid sequence having a (Gly Ala Pro Gly Ala Pro Gly Ser Gln Gly Ala Pro Gly Leu Gln)p (SEQ ID NO: 68) sequence includes amino acid sequences represented by SEQ ID NOs: 49 to 51.

The auxiliary amino acid sequence having a (Gly Ala Pro Gly Thr Pro Gly Pro Gln Gly Leu Pro Gly Ser Pro)q (SEQ ID NO: 69) sequence includes amino acid sequences represented by SEQ ID NOs: 52 to: 54.

Among these amino acid sequences, preferred are amino acid sequences represented by SEQ ill NO:9, to, 12, 13, 14, 15, 16, 18, 19, 21, 22, 24, 25, 26, 27, 28, 30, 31, 32, 34, 35, 37, 38, 40, 41, 43, 44, 46, 47, 49, 50, 52, or 53, more preferably amino acid sequences represented by SEQ ID NO: 10, 12, 13, 14, 16, 19, 22, 26, 27, 28, 29, 30, 32, 35, 38, 41, 44, 47, 50, or 53, and particularly preferably amino acid sequences represented by SEQ ID NO:12, 13, or 30. The polypeptide (P) may include a branched chain, may be partially crosslinked, or may include a ring structure. However, preferably the polypeptide (P) is not crosslinked, more preferably is a linear-chain structure that is not crosslinked, and particularly preferably is a linear-chain structure that does not have a ring structure and is not crosslinked. The linear-chain structure includes a β structure (secondary structure where a linear peptide is folded, and the folded parts are lined up in parallel, between which hydrogen bonds are formed).

From the viewpoints of cell-adhering property, thermal resistance, etc., preferably the polypeptide (P) has a structure where a minimum amino acid sequence (X) and an auxiliary amino acid sequence (Y) are alternately chemically bonded. In this case, from the viewpoints of cell-adhering property etc., the number of repeated units (X-Y) of the minimum amino acid sequence (X) and the auxiliary amino acid sequence (Y) is preferably 1 to 50, more preferably 2 to 40, particularly preferably 3 to 30, and most preferably 4 to 20.

Moreover, the content numbers of minimum amino acid sequences (X) and auxiliary amino acid sequences (Y) may be the same or different. If they are different, preferably either one of the content numbers thereof is smaller than the other number by one (in this case, the number of the auxiliary amino acid sequences (Y) is preferably smaller). The content ratio (X/Y) of the number of minimum amino acid sequences (X) to the number of auxiliary amino acid sequences (Y) in the polypeptide (P) is preferably 0.66 to 1.5, more preferably 0.9 to 1.4, and particularly preferably 1 to 1.3.

Moreover, the terminal site of the polypeptide (P) (from the minimum amino acid sequence (X) or the auxiliary amino acid sequence (Y) to the peptide terminal) may contain another amino acid. If another amino acid is contained, the content thereof is preferably 1 to 1000 per polypeptide, more preferably 3 to 300, and particularly preferably 10 to 100.

The number-average molecular weight (Mn) of the polypeptide (P) is preferably 1,000 to 1,000,000, more preferably 2,000 to 700,000, particularly preferably 3,000 to 400,000, and most preferably 4,000 to 200,000. The number-average molecular weight (Mn) of the polypeptide may be obtained by a publicly known method such as a method of separating a measurement sample (such as polypeptide) by SDS-PAGE (SDS polyacrylamide gel electrophoresis), and comparing the migration distance thereof with that of a reference material (hereunder the same).

Hereunder are preferred examples of the polypeptide (P).
(1) A case where the minimum amino acid sequence (X) is an Arg Gly Asp (SEQ ID NO: 70) sequence (x1):

A polypeptide of about 110,000 Mn having a structure where 13 (x1) and 13 (Gly Ala Gly Ala Gly Ser)g (SEQ ID NO: 13) sequences (13)(y1) are alternately chemically bonded ("ProNectin F", ProNectin: registered trademark (Japan and US), manufactured by Sanyo Chemical Industries. (hereunder the same));

A polypeptide of about 20,000 Mn having a structure where 5 (x1) and 5 (Gly Ala Gly Ala Gly Ser)3 (SEQ ID NO: 74) sequences (12)(y2) are alternately chemically bonded ("ProNectin F2");

A polypeptide of about 10,000 Mn having a structure where 3 (x1) and 3 (Gly Val Pro Gly Val)2 Gly Gly (Gly Ala Gly Ala Gly Ser)3 (SEQ ID NO: 71) sequences (30)(y3) are alternately chemically bonded ("ProNectin F3"); and the like.
(2) A case where the minimum amino acid sequence (X) is a Ile Lys Val Ala Val (SEQ ID NO: 7) sequence (x2):

"ProNectin L", "ProNectin L2", or "ProNectin L3" where the Arg Gly Asp (SEQ ID NO: 70) sequence (x1) of ProNectin F, ProNectin F2, or ProNectin F3 is changed into a Ile Lys Val Ala Val (SEQ ID NO: 7) sequence (7)(x2), and the like.

(3) A case where the minimum amino acid sequence (X) is a Tyr Ile Gly Ser Arg (SEQ ID NO: 2) sequence (x3):

"ProNectin Y", "ProNectin Y2", or "ProNectin Y3" where the Arg Gly Asp (SEQ ID NO: 70) sequence (x1) of ProNectin F, ProNectin F2, or ProNectin F3 is changed into a Tyr Ile Gly Ser Arg (SEQ ID NO: 2) sequence (x3), and the like.

Moreover, in addition to the polypeptides of (1) to (3), there may be also preferably used RetroNectin (recombinant human fibronectin CH-296) manufactured by Takara (a polypeptide of about 60,000 Mn having an Arg Gly Asp (SEQ ID NO: 70) sequence (x1) and a Leu Asp Val (SEQ ID NO: 73) sequence as the minimum amino acid sequence (X<<, and RGDS-Protein A ("RGDS" disclosed as SEQ ID NO: 75) manufactured by Takara (a polypeptide of about 30,000 Mn having an Arg Gly Asp (SEQ ID NO: 70) sequence (x1) as the minimum amino acid sequence (X), where these polypeptides do not contain an auxiliary amino acid sequence (Y). Therefore, the thermal resistance and the like thereof are inferior to those of the abovementioned (1) to (3).

Moreover, the amino acid sequences of these polypeptides are disclosed in Japanese Unexamined Patent Publication No. H2-311498 (the contents of U.S. Pat. No. 5,198,423A are incorporated in the present application by reference).

The method of manufacturing the polypeptide (P) is not specifically limited, and it may be manufactured in the same manner as an already known method for synthesizing a peptide, and it may be synthesized by for example an organic synthesis method (such as a solid phase synthesis method and a liquid phase synthesis method), a biochemical synthesis method [genetic recombinant bacteria (such as yeast, bacteria, and $E.\ coli$)], and the like. Regarding the organic synthesis method, there may be used a method described in for example "Lectures on Biochemical Experiments, Second Series, 2, Chemistry of Proteins Vol. 2" pages 641-'694, edited by The Japanese Biochemical Society, (published by Tokyo Kagaku Dojin; 20 May 1987), and the like. Regarding the biochemical synthesis method, there may be used methods described in, for example, Published Japanese translation No. H3-502935 of PCT International Publication (the contents of U.S. Pat. No. 5,243,038A, U.S. Pat. No. 5,496,712A, U.S. Pat. No. 5,514,581A, U.S. Pat. No. 5,606,019A, U.S. Pat. No. 5,641,648A, U.S. Pat. No. 5,723,588A, U.S. Pat. No. 5,770,697A, U.S. Pat. No. 5,773,249A, U.S. Pat. No. 5,808,012A, U.S. Pat. No. 5,830,713A, US6018030A, U.S. Pat. No. 6,140,072A, U.S. Pat. No. 6,184,348B1, U.S. Pat. No. 6,355,776B1, U.S. Pat. No. 6,380,154B1, US2003083464A1, and US2003176355A1 are incorporated in the present application by reference), and the like. From the point of being able to readily synthesize the polypeptide (P) of a high molecular weight, preferred is a biochemical synthesis method using genetic recombinant bacteria, and particularly preferred is a synthesis method using genetic recombinant $E.\ coli$. ff the support contains the polypeptide (P), the (P) may be contained in the surface of the support, and the (P) is bonded to the surface of the support by a chemical bond (such as an ionic bond, a hydrogen bond, and/or a covalent bond) and/or a physical adsorption (adsorption by Van der Waals force). Among these, preferred is a chemical bond, and more preferred is a covalent bond.

The reaction for covalently bonding the polypeptide (P) to the support can be performed by a publicly known method. Examples thereof include methods described in "Fundamentals and Experiments of Peptide Synthesis" published by Maruzen (5 Oct. 1997). More specifically these are as in (1) to (3) hereunder.

(1) In the case where a polypeptide having a primary amino group or a secondary amino group and a support not containing a polypeptide (P) (hereunder, P non-contained support) but having a carboxyl group are subject to reaction, the carboxyl group of the P non-contained support is previously reacted with a carbodiimide compound, so as to obtain acylisourea (R'N=C(OCOR)—NH—R' (—OCOR is the site derived from the support)). Then, by adding the polypeptide having a primary amino group or a secondary amino group to this acylisourea, the P non-contained support and the polypeptide can be amide bonded.

The carbodiimide compound includes N,N'-dicyclohexylcarbodiimide, 1-ethyl-3-(3dimethylaminopropyl) carbodiimide hydrochloride, and the like.

(2) In the case where a polypeptide having a primary amino group or a secondary amino group and a P non-contained support having a hydroxyl group are subject to reaction, the hydroxyl group of the P non-contained support is previously reacted with a carbonyldiimidazole compound, so as to obtain an imidazole derivative (R-Im, where Im denotes an imidazoline ring and R is derived from the support). Then, by adding the polypeptide having a primary amino group or a secondary amino group to this imidazole derivative, the P non-contained support and the polypeptide can be N—C bonded.

The carbonyldiimidazole compound includes N,N'-carbonyldiimidazole, and the like.

(3) In the case where a polypeptide having a hydroxyl group and a P non-contained support having a carboxyl group are subject to reaction, the carboxyl group of the P non-contained support is previously reacted with a carbodiimide compound, so as to obtain acylisourea. Then, by adding the polypeptide having a hydroxyl group to this acylisourea, the P non-contained support and the polypeptide can be ester bonded.

The methods of physically adsorbing, ionically bonding, and/or hydrogen-bonding a polypeptide to a P non-contained support include a production method of putting the polypeptide and the P non-contained support into a solvent or the like, and mixing them. The solvent is not specifically limited. However, there may be used water (such as tap water, ion exchanged water, distilled water, and ion exchanged distilled water) as well as an aqueous solution containing inorganic salt, organic acid salt, acid and/or base (for example, Japanese Unexamined Patent Publication No. 2003-189848), and the like. The contents (weight %) of inorganic salt, organic acid salt, acid and base is preferably 0.001 to 50 based on the weight of the aqueous solution, more preferably 0.005 to 30, and particularly preferably 0.01 to 10.

Among these solvents, preferred are water and aqueous solution containing inorganic salt, acid and/or base, more preferably ion exchanged distilled water and aqueous solution containing inorganic salt, acid and/or base, and particularly preferably aqueous solution containing inorganic salt, acid and/or base.

If the support contains the polypeptide (P), the content ($\mu g/cm^2$) of the polypeptide (P) is preferably 0.0001 to 100000 per 1 $cm^2$ of the mean surface area of the support, more preferably 0.001 to 10000, and particularly preferably 0.01 to 1000. Within this range, the efficiency of cell culture is further improved.

The content of the polypeptide (P) can be obtained as follows.

(1) The content ($\mu g/g$) of the polypeptide (P) per unit weight of the support is measured by for example an immunoassay (described in Japanese Unexamined Patent Publication No. 2004-049921 and the like). That is, the support and an antibody which is bindable to the polypeptide (P) and labeled with an enzyme (hereunder, enzyme labeled antibody 1) are reacted, then the enzyme level of the reacted enzyme labeled antibody 1 is measured, and thereby the content of the polypeptide (P) per unit weight is measured.

(2) Next, using a surface shape measuring microscope (3D shape measuring microscope utilizing the confocal principle, such as VK-9500 manufactured by Keyence Corporation), three dimensional data of the shape of the top surface (for example, 20 µm×20 µm) of the support fixed to a slide glass with an adhesive or the like (hereunder, fixed support), is obtained. Then, small pore (having a diameter of less than 1 µm) parts are uniformly excluded from this three dimensional data (corrected as a flat surface) so as to obtain the partial surface area (A) of the support having ribs (ridges) and the like. Moreover, small pore (having a diameter of less than 1 µm) parts, ribs (ridges), and the like are uniformly excluded from the three dimensional data of the surface shape (corrected as a flat surface) so as to obtain the partial surface area (B) of the support having a flat surface. Furthermore, the three dimensional data of 9 supports are measured in the same manner, to obtain the partial surface areas (A) of these supports and the partial surface areas (B) of these supports. For these 10 supports, the mean partial surface area (HA) of the partial surface areas (A) of the supports having ribs and the like, and the mean partial surface area (HB) of the partial surface areas (B) of the supports having flat surfaces are calculated.

If the support is globular, the mean surface area per unit weight of the support is calculated from an equation (mean surface area per unit weight $(cm^2/g) = [4 \times \pi \times (ra/2/10000)^2 i]/[4/3 \times \pi \times (ra/2/10000)^3 \times d] \times [(HA)/(HB)])$, where ra denotes a particle diameter of the support, and d denotes a true specific gravity of the support.

If the support is non-globular (rod, hexahedron, or plate shape) or porous, disenabling the calculation of the above method, the mean surface area per unit weight of the support is calculated as follows.

Using a specific surface area meter (for example, QUANTASORB manufactured by Yuasa Ionics Inc.), the surface area of the support is measured (measurement gas; He/Kr=99.9/0.1 in volume ratio, detection gas; nitrogen). The mean surface area per unit weight $(cm^2/g)$ of the support is calculated from an equation (surface area of support/weight of support).

(3) The content of the polypeptide (P) per unit weight (µg/g) is divided by the mean surface area per unit weight $(cm^2/g)$ to calculate the content per 1 $cm^2$ of the mean surface area of the support $(\mu g/cm^2)$.

The cell dispersing agent means a cell dispersing agent free from animal-origin components used for subculture, and used for the purpose of detaching cells from the support. The cell dispersing agent includes a chelating agent (such as EDTA), a serum-free medium at 2 to 30° C., a protease originated from a plant (such as papain), a protease originated from genetic recombinant bacteria (trypsin-like enzyme (such as rProtease manufactured by Invitrogen)), and the combination thereof. Among these, from the viewpoints of detachability of cells from the support etc., preferred are a protease originated from a plant, a protease originated from genetic recombinant bacteria, and the combination thereof, and more preferably a protease originated from genetic recombinant bacteria.

In the method of producing a virus of the present invention, a large amount of virus can be produced by: adhering adhesive cells to a support free from animal-origin components; culturing the adhesive cells in a medium free from animal-origin components; subculturing the cultured adhesive cells using a cell dispersing agent free from animal-origin components; and then inoculating and proliferating a virus in the cells obtained by culturing the adhesive cells.

The culture (hereunder, preculture) for obtaining the adhesive cells used for cell dissemination is not specifically limited, and there may be used anyone of materials containing animal-origin components (such as a support, a medium, and a cell dispersing gent), and materials free from animal-origin components (such as a support, a medium, and a cell dispersing agent). However, in the preculture, there are preferably used only materials free from animal-origin components (such as a support, a medium, and a cell dispersing agent).

The method of adhering the adhesive cells obtained by the preculture to the support may be a normal method, and there may be applied a method of disseminating the cells in a medium or a support, and the like.

The dissemination amount of the adhesive cells $(10^4/cm^2)$ is determined according to the type of the adhesive cell. However, preferred is 0.001 to 1000 per 1 $cm^2$ of the mean surface area of the support, more preferably 0.01 to 100, and particularly preferably 0.1 to 10. The method of measuring the number of the adhesive cells is not specifically limited, however for example the number of cell nuclei may be measured by a cell nucleus counting method using a crystal violet by Wezel. Moreover, the cell density in a medium $10^4/mL$) is preferably 0.01 to 10000 per 1 mL of medium, more preferably 0.1 to 1000, particularly preferably 1 to 100, even more particularly preferably 5 to 50, and most preferably 10 to 30.

The incubation period (day) for the adhesive cells is preferably 3 to 30, more preferably 4 to 21, particularly preferably 5 to 15, still more preferably 6 to 10, and most preferably 7 or 8. Although it varies depending on the type of the adhesive cell, in the case of an 8 days culture, the cell density in a medium increases about 3 to 30 times compared to that at the time of starting the culture.

From ⅓ to all of the amount of the medium is preferably exchanged every 1 to 5 days. The density of carbon dioxide during the incubation (volume %) is preferably 2 to 10 based on the volume of the incubation atmosphere, more preferably 4 to 6, and particularly preferably 5.

The incubation temperature (° C.) is preferably 25 to 42, more preferably 30 to 40, particularly preferably 35 to 39, and most preferably 37.

If a microcarrier (particle diameter; 20 to 500 µm, surface area; 100 $cm^2$ to 100 $m^2$, or the like) is used as the support, there may be used (1) a spinner flask or a vessel, (2) a radial flow type rector, etc., as a culture vessel.

(1) If a spinner flask, a vessel, or the like is used, there may be applied, for example, a method of putting adhesive cells, a microcarrier, and a medium into the culture vessel (volume; 100 mL to 100 L or the like), and culturing while stirring.

(2) If a radial flow type rector or the like is used, there may be applied, for example, a method of setting a microcarrier in the culture vessel (total volume; 100 mL to 100 L or the like), then culturing while circulating the medium containing the adhesive cells.

On the other hand, if a hollow fiber (inner diameter: 10 to 500 !Jill or the like) is used as the support, there may be applied, for example, a method of adding a medium containing the adhesive cells into a cartridge (total capacity; 10 mL to 10 L or the like), then culturing while circulating the medium in the hollow fiber.

Moreover, if a roller bottle (total capacity"; 0.1 to 20 L or the like) is used as the support, there may be applied, for example, a method of adding a medium containing the adhesive cells into the culture vessel, then culturing while stirring.

The subculture using a cell dispersing agent means to make the adhesive cells obtained from the culture in the above manner, into a cell dispersion by the cell dispersing agent, and then performing the culture of the adhesive cells again using this cell dispersion.

The timing for inoculating the virus in the cells obtained by culturing the adhesive cells is preferably between the 3rd to 30th day from the start of culturing the adhesive cells, more preferably between the 4th to 21st day, particularly preferably between the 5th to 15th day, still more preferably between the 6th to 10th day, and most preferably between the 7th and 8th day. Moreover, the cell density (104/mL) of the cultured cells for inoculating the virus is preferably 0.2 to 200000, more preferably 2 to 20000, particularly preferably 20 to 2000, even more particularly preferably 100 to 1000, and most preferably 200 to 500.

The medium is preferably exchanged with a serum-free medium prior to the inoculation of the virus. More preferably, the medium of the cell culture is removed, and PBS (0.02M phosphate buffer solution or the like) and/or a serum-free medium are added, which is stirred for 1 minute to 1 hour. Then, the added PBS and/or serum-free medium are removed, and the serum-free medium is added.

This serum-free medium is preferably the same one that has been used for the cell culture.

This serum-free medium mayor may not contain a cell dispersing agent. In the case of an Influenza virus, preferably the serum-free medium contains a cell dispersing agent. If the serum-free medium contains a cell dispersing agent, the content thereof (volume %) is preferably 0.5 to 40 based on the volume of the serum-free medium, more preferably 1 to 20, and particularly preferably 2 to 10.

The M.O.I. (multiplicity of infection) for inoculating the virus varies depending on the types of cell and virus, however preferred is 1 to 0.0000001, more preferred is 0.1 to 0.00001, and particularly preferred is 0.05 to 0.0001.

The incubation period (growth period; day) of the virus is preferably 2 to 14, and more preferably 3 to 10.

The incubation temperature (growth temperature; ° C.) of the virus is preferably 30 to 39, more preferably 32 to 38, and particularly preferably 33 to 37.

The pH of the medium is preferably controlled within a fixed range, and the range is preferably 6 to 9, more preferably 6.5 to 8.5, and particularly preferably 7 to 8.

The vaccine that can be produced using the method of producing a virus of the present invention is not specifically limited. However, preferred are a Japanese encephalitis vaccine, a Dengue fever vaccine, a West Nile fever vaccine, an Influenza vaccine, a Rabies vaccine, a Varicella vaccine, a Polio vaccine, a Hepatitis A vaccine, a Measles vaccine, a Rubella vaccine, and a Mumps vaccine, more preferred are a Japanese encephalitis vaccine, a Dengue fever vaccine, a West Nile fever vaccine, an Influenza vaccine, a Polio vaccine, a Measles vaccine, a Rubella vaccine, and a Mumps vaccine, particularly preferred are an Influenza vaccine, a Measles vaccine, a Rubella vaccine, and a Mumps vaccine, and most preferred is an Influenza vaccine.

According to the present invention, since culture materials free from animal-origin components are used in the process of cell culture and virus production, a large amount of adhesive cells which are safe and stable quality, can be cultured. Furthermore, it has advantages in that it can minimize the likelihood of contamination due to foreign substances, it is free from unknown infectious agents, and thus there is no need of performing a treatment for deactivating the infectious agent.

The present invention is not limited to the above contents of description, and various modification can be made within the scope of the present invention.

Hereunder is a detailed description of the present invention, with reference to Examples and drawings. However, the present invention is not limited to these Examples.

<Culture for Obtaining Adhesive Cell Used for Cell Dissemination>

Vero during preculture in Dulbecco's minimum essential medium (DMEM) medium+5 volume % fetal bovine serum (FBS) (manufactured by Invitrogen) were dispersed by a diluted solution having a cell dispersing agent (rProtease (registered trademark) manufactured by Invitrogen) diluted with PBS as required, under a condition of 37° C., and the filtrate was removed by centrifugation, to obtain the Vero (S) for cell dissemination.

Example 1

Production of Japanese Encephalitis Virus Using Serum-Free Medium and ProNectin F-Bonded Nylon Beads (1) ProNectin F was diluted with phosphate buffer solution (PBS) so that the density of ProNectin F became 300 µg/ml, to produce ProNectin F solution. 100 ml of water-soluble carbodiimide solution (1-ethyl-3-(3-dimethylaminopropyl) carbodiimide hydrochloride (300 mM aqueous solution manufactured by Dozind) was added with 50 g of 12 nylon beads (particle diameter 150 to 250 µm, manufactured by Trial Corporation), and stirred by a stirrer for 2 hours. Then, 100 ml of phosphate buffer solution (pH=7.2) was added thereinto and the solution was removed by means of suction. This operation was performed 5 times (washing), and thereby carbodiimide bonded nylon beads (1) were obtained. Next, these carbodiimide bonded nylon beads (1) were soaked in 100 ml of ProNectin F solution, and stirred for 2 hours. Then, 100 ml of phosphate buffer solution (pH=7.2) was added thereinto, and the solution was removed by means of suction. This operation was performed 3 times (washing), and then it was stirred in ammonia aqueous solution (300 mM, 100 ml) for 2 hours. Then, 100 ml of ion exchanged water was added, and the solution was removed by means of suction. This operation was performed for 3 times (washing). Next, it was dried by blowing hot wind of 100° C. for 60 minutes, and ProNectin F-bonded nylon beads (ProNectin F bonding amount: 0.3 µg/cm$^2$) were obtained.

(2) A sample 4 comprising a serum-free medium (VP-SFM manufactured by fuvitrogen) free from animal-origin components and ProNectin F-bonded nylon beads free from animal-origin components was put into a spinner flask (F7689 manufactured by Techne Incorporated).

Next, the Vero (S) for cell dissemination were disseminated in the spinner flask containing the sample 4 so that the cell density became 2×10$^5$ cells/mL, so as to make the operation volume (M) 100 mL. Then, the culture solution containing the cells, the medium, and the microcarrier was stirred at 25 rpm so as to adhere the cells to the microcarrier. Then, the cells were cultured using a magnetic stirrer (MCS-104L manufactured by Techne Incorporated) at a stirring rotational speed of 25 rpm to 35 rpm in a thermostatic chamber at 37° C. for 24 days.

The subculture of the cells was performed every 8 days. From the 3rd day of the cell dissemination, 50 volume % of medium was exchanged every day. The cells were dispersed by a diluted solution having a cell dispersing agent free from animal-origin components (rProtease (registered trademark)

manufactured by Invitrogen) 5-fold diluted with PBS, under a condition of 37° C., and the filtrate was removed by centrifugation. Then, the required amount thereof was disseminated in a spinner flask that had been previously prepared, so as to perform the subculture operation.

The change in the cell density of the sample 4 with time was obtained by a general method such as hematometry and microscopy. A graph showing the cell density (cells/mL) on the y-axis and time on the x-axis, is shown in FIG. 1.

On the 24th day from the start of the cell culture, the culture solution in the spinner flask was removed, and washing with PBS was performed twice. Then, Japanese encephalitis virus (JEV) was inoculated at M.O.I=0.01, and cultured at a stirring rotational speed of 35 rpm in a thermostatic chamber at 37° C. On the 2nd day of the JEV culture, 1.5 mL of 7.5 volume % sodium hydrogen carbonate solution was added into each spinner flask, so as to make pH 7.2.

Figure 2:
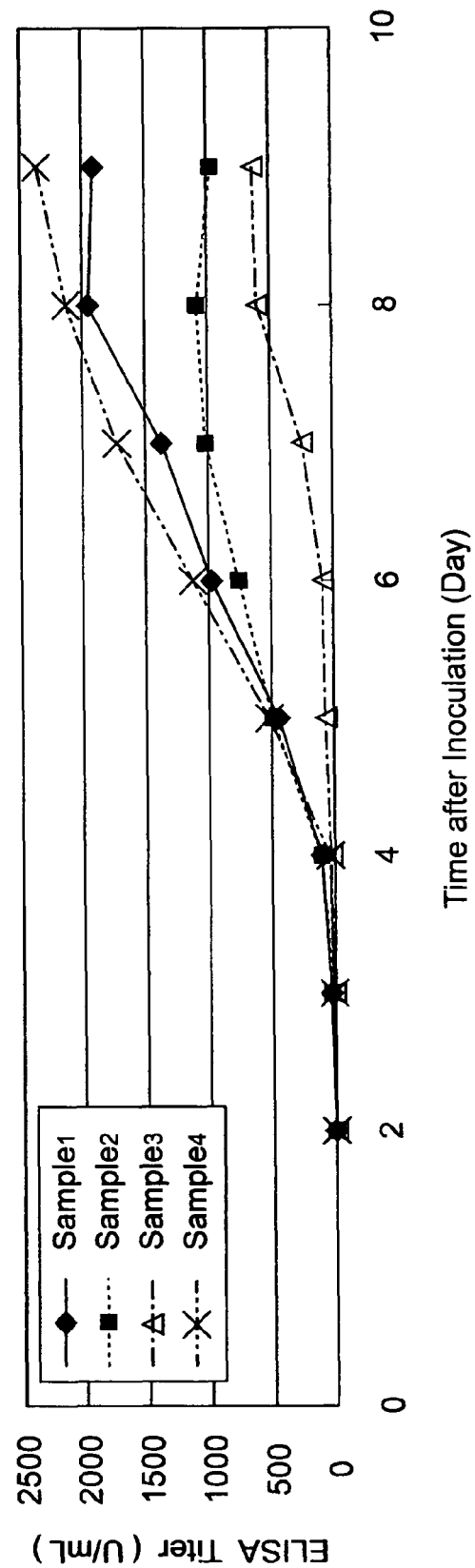
FIG. 2 is a graph showing changes in virus production quantity by ELISA with time in Example 1 and Comparative Examples 1 to 3.
Figure 3:
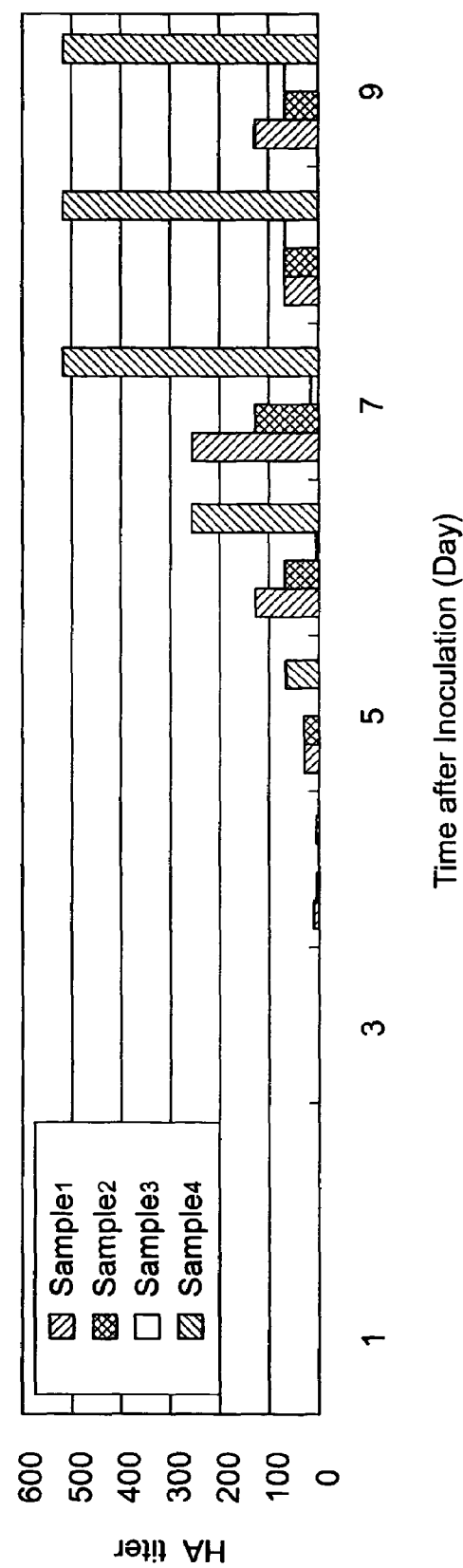
FIG. 3 is a graph showing changes in virus production quantity by HA with time in Example 1 and Comparative Examples 1 to 3.

Sampling was performed between the 2nd to 8th day of the JEV culture, and the number of cells was measured by measuring the number of nuclei after citric acid treatment. Regarding the index of JEV growth, (1) HA (Hemagglutination) value was measured according to the usual method, and (2) in ELISA (Enzyme-linked immunosorbent assay), antibody purification of anti-JEV antiserum was performed by means of protein A column and the reaction specificity was confirmed by means of Western Blotting, and then the purified antibodies were labeled with peroxidase, so as to construct a sandwich ELISA. Regarding the ELISA value, the autologous value from reference Japanese encephalitis vaccine Beijing strain Lot. 197-P was added, and the purified inactive JEV solution was used as a reference antigen. A graph showing the change in the JEV production quantity with time by ELISA, is shown in FIG. 2. A graph showing the change in the JEV production quantity with time by HA, is shown in FIG. 3. Moreover, the highest values of ELISA and HA measurement values are shown in Table 1.

TABLE 1

|  | Cell number at time of virus inoculation (×10$^6$ cells/mL) | HA | ELISA (U/mL) |
| --- | --- | --- | --- |
| Sample 1 | 1.6 | 256 | 1949 |
| Sample 2 | 3 | 128 | 1087 |
| Sample 3 | 2.4 | 64 | 626 |
| Sample 4 | 3 | 512 | 2367 |

Comparative Example 1

Production of Japanese Encephalitis Virus Using Serum Medium and Dextran Beads

Product Name: Cytodex1 Manufactured by Amersham

The virus was produced in the same manner as that of Example 1, except that a sample 1 {serum medium (DMEM medium+5 volume % FBS), and dextran beads free from animal-origin components} was used instead of the sample 4 that has been described in Example 1.

Comparative Example 2

Production of Japanese Encephalitis Virus Using Serum-Free Medium and Dextran Beads Product Name: Cytodex1 Manufactured by Amersham The virus was produced in the same manner as that of Example 1, except that a sample 2 {serum-free medium (VP-SFM manufactured by Invitrogen) free from animal-origin components, and dextran beads free from animal-origin components} was used instead of the sample 4 that has been described in Example 1.

Comparative Example 3

Production of Japanese Encephalitis Virus Using Serum-Free Medium and Dextran Beads Coated with Denatured Pig Collagen Product Name: Cytodex3 Manufactured by Amersham The virus was produced in the same manner as that of Example 1, except that a sample 3 {serum-free medium (VP-SFM manufactured by Invitrogen) free from animal-origin components, and dextran beads coated with denatured pig collagen} was used instead of the sample 4 that has been described in Example 1.

For Comparative Examples 1 to 3, in the same manner as that of Example 1, the number of cells at the time of virus inoculation, and the highest values of ELISA and HA measurement values are shown in Table 1. A cell density-time graph is shown in FIG. 1. An ELISA Titer-day graph is shown in FIG. 2. A HA Titer-day graph is shown in FIG. 3.

From FIG. 1 and Table 1, it can be seen that the cell density of Example 1 (sample 4) was the highest on the 8th, 16th, and 24th day from the start of the culture, and the cells of Example 1 (sample 4) were stably and efficiently grown compared to Comparative Example 1 (sample 1), Comparative Example 2 (sample 2), and Comparative Example 3 (sample 3). Moreover, from FIG. 2, FIG. 3, and Table 1, it can be seen that Example 1 (sample 4) showed higher values of both ELISA and HA compared to Comparative Example 1 (sample 1), Comparative Example 2 (sample 2), and Comparative Example 3 (sample 3), and Japanese encephalitis virus were efficiently grown.

Example 2

Production of Influenza Virus Using Serum-Free Medium and ProNectin F-Bonded Nylon Beads A sample 8 comprising a VP-SFM medium and ProNectin F-bonded nylon beads was put into a spinner flask (F7689 manufactured by Techne Incorporated).

Next, the Vero (S) for cell dissemination were disseminated in the spinner flask containing the sample 8 so that the cell density became 2×10$^5$ cells/mL, so as to make the operation volume (M)100 mL. Then, the culture solution containing the cells, the medium, and the microcarrier was stirred at 35 rpm so as to adhere the cells to the microcarrier. Then, the cells were cultured using a magnetic stirrer (MODEL1104M manufactured by Wakenyaku Co. Ltd.) at a stirring rotational speed of 35 rpm in a thermostatic chamber at 37° C. for 24 days.

The subculture of the cells was performed every 8 days. From the 3rd day of the cell dissemination, 50 volume % of medium was exchanged every day. The cells were dispersed by rProtease that had been used for the cell subculture, under a condition of 37° C., and the filtrate was removed by centrifugation. Then, the required amount thereof was disseminated in a spinner flask that had been previously prepared, so as to perform the subculture operation.

Regarding the cell washing process, on the 24th day from the start of the cell culture, the stirring of the spinner flask was stopped, the culture solution was removed therefrom, 50 mL of PBS was added therein, and the flask was stirred in a thermostatic chamber at 33° C. for 20 minutes. Next, the cell washing operation was performed in the same condition, but with a VP-SFM medium. Then, the VP-SFM medium was removed, and another VP-SFM medium was newly added into the spinner flask to make the volume 95 mL. 5 mL of rProtease was added into this spinner flask and influenza virus (B/Johannesburg/5/99) was inoculated at M.O.I=0.001. The influenza virus was cultured at a stirring rotational speed of 35 rpm in a thermostatic chamber at 33° C., while the cap of the spinner flask was loosened. After the influenza virus was inoculated, the pH of the medium was kept at pH7.2 to pH7.8 with a 7.5 volume % sodium hydrogencarbonate solution (0.4 mL of 7.5 volume % sodium hydrogencarbonate solution was added after 18 hours of the influenza virus culture, and 0.6 mL thereof was added after 42 hours in the same manner). Sampling was performed after 67 hours of the influenza virus culture. The HA method using avian red blood corpuscle was used as an index of the influenza virus growth, and the HA value was 128 times.

Example 3

Production of Influenza Virus Using Serum-Free Medium and ProNectin F2-Bonded Nylon Beads The virus was produced in the same manner as that of Example 2, except that ProNectin F2-bonded nylon beads were used instead of the ProNectin F-bonded nylon beads that have been described in Example 2 {proNectin F2 bonding amount: 0.3 µg/cm$^2$, the beads were produced in the same manner as that of the ProNectin F-bonded nylon beads, except that ProNectin F2 was used instead of ProNectin F.) The HA value obtained in the same matter as that of Example 2 was 128 times.

Example 4

Production of Influenza Virus Using Serum-Free Medium and ProNectin F3-Bonded Nylon Beads The virus was produced in the same manner as that of Example 2, except that ProNectin F3-bonded nylon beads were used instead of the ProNectin F-bonded nylon beads that have been described in Example 2 (proNectin F3 bonding amount: 0.2 µg/cm$^2$, the beads were produced in the same manner as that of the ProNectin F-bonded nylon beads, except that ProNectin F3 was used instead of ProNectin F.) The HA value obtained in the same matter as that of Example 2 was 128 times.

Comparative Example 4

Production of Influenza Virus Using Serum Medium and Dextran Beads

Product Name: Cytodex1 Manufactured by Amersham

The virus was produced in the same manner as that of Example 2, except that a sample 5 {serum medium (DMEM medium+5 volume % FBS), and dextran beads free from animal-origin components} was used instead of the sample 8 that has been described in Example 2. The HA value obtained in the same matter as that of Example 2 was 32 times.

Comparative Example 5

Production of Influenza Virus Using Serum-Free Medium and Dextran Beads

Product Name: Cytodex1 Manufactured by Amersham

The virus was produced in the same manner as that of Example 2, except that a sample 6 {serum-free medium (VP-SFM manufactured by Invitrogen) free from animal-origin components, and dextran beads free from animal-origin components} was used instead of the sample 8 that has been described in Example 2. The HA value obtained in the same matter as that of Example 2 was 4 times.

Comparative Example 6

Production of Influenza Virus Using Serum-Free Medium and Dextran Beads Coated with Denatured Pig Collagen Product Name: Cytodex1 Manufactured by Amersham The virus was produced in the same manner as that of Example 2, except that a sample 7 {serum-free medium (VP-SFM manufactured by Invitrogen) free from animal-origin components, and dextran beads coated with denatured pig collagen} was used instead of the sample 8 that has been described in Example 2. The HA value obtained in the same matter as that of Example 2 was 4 times.

HA values were much higher in Example 2, Example 3, and Example 4 compared to Comparative Example 4, Comparative Example 5, and Comparative Example 6, and it can be seen that the influenza virus was very effectively grown.

[Sequence Table]

The invention claimed is:

1. A method of producing a virus comprising:
adhering adhesive cells to a support which has a polypeptide of about 20,000 Mn having a structure where 5 (Arg Gly Asp) sequences (SEQ ID NO: 70) and 5 (Gly Ala Gly Ala Gly Ser)$_3$ sequences (SEQ ID NO: 74) are alternately chemically bonded, and is free from animal-origin components;
culturing the adhesive cells in a medium free from animal-origin components;
subculturing the cultured adhesive cells using a cell dispersing agent that is free from animal-origin components and is a protease originated from a plant, a protease originated from genetically recombinant bacteria, or a combination thereof; and then
inoculating and proliferating a virus in the cells obtained by culturing the adhesive cells, thereby improving efficiency for producing a virus.

2. The method according to claim 1, wherein said virus belongs to at least one selected from a group consisting of Flaviviridae, Orthomyxoviridae, Adenoviridae, Herpesviridae, Picornaviridae, Paramyxoviridae, Togaviridae, and Poxviridae.

3. The method according to claim 1 or 2, wherein said support is a microcarrier.

4. A method of producing a virus comprising:
adhering adhesive cells to a support which has a polypeptide of about 10,000 Mn having a structure where 3 (Arg Gly Asp) sequences (SEQ ID NO: 70) and 3 (Gly Val Pro Gly Val)$_2$ Gly Gly (Gly Ala Gly Ala Gly Ser)$_3$ sequences (SEQ ID NO: 71) are alternately chemically bonded, and is free from animal-origin components;
culturing the adhesive cells in a medium free from animal-origin components;
subculturing the cultured adhesive cells using a cell dispersing agent that is free from animal-origin components and is a protease originated from a plant, a protease originated from genetically recombinant bacteria, or a combination thereof; and then
inoculating and proliferating a virus in the cells obtained by culturing the adhesive cells, thereby improving efficiency for producing a virus.

5. The method according to claim 4, wherein said virus belongs to at least one selected from a group consisting of Flaviviridae, Orthomyxoviridae, Adenoviridae, Herpesviridae, Picornaviridae, Paramyxoviridae, Togaviridae, and Poxviridae.

6. The method according to claim 4 or 5, wherein said support is a microcarrier.

* * * * *

```
SEQUENCE LISTING

<160> NUMBER OF SEQ ID NOS: 75

<210> SEQ ID NO 1
<211> LENGTH: 4
<212> TYPE: PRT
<213> ORGANISM: Homo sapiens

<400> SEQUENCE: 1

Arg Glu Asp Val
1
```

```
<210> SEQ ID NO 2
<211> LENGTH: 5
<212> TYPE: PRT
<213> ORGANISM: Homo sapiens

<400> SEQUENCE: 2

Tyr Ile Gly Ser Arg
1               5

<210> SEQ ID NO 3
<211> LENGTH: 5
<212> TYPE: PRT
<213> ORGANISM: Homo sapiens

<400> SEQUENCE: 3

Pro Asp Ser Gly Arg
1               5

<210> SEQ ID NO 4
<211> LENGTH: 7
<212> TYPE: PRT
<213> ORGANISM: Homo sapiens

<400> SEQUENCE: 4

Arg Tyr Val Val Leu Pro Arg
1               5

<210> SEQ ID NO 5
<211> LENGTH: 6
<212> TYPE: PRT
<213> ORGANISM: Homo sapiens

<400> SEQUENCE: 5

Leu Gly Thr Ile Pro Gly
1               5

<210> SEQ ID NO 6
<211> LENGTH: 10
<212> TYPE: PRT
<213> ORGANISM: Homo sapiens

<400> SEQUENCE: 6

Arg Asn Ile Ala Glu Ile Ile Lys Asp Ile
1               5                   10

<210> SEQ ID NO 7
<211> LENGTH: 5
<212> TYPE: PRT
<213> ORGANISM: Homo sapiens

<400> SEQUENCE: 7

Ile Lys Val Ala Val
1               5

<210> SEQ ID NO 8
<211> LENGTH: 4
<212> TYPE: PRT
<213> ORGANISM: Homo sapiens

<400> SEQUENCE: 8

Asp Gly Glu Ala
1

<210> SEQ ID NO 9
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 9

Gly Ala Gly Ala Gly Ala Gly Ala Gly Ala
1               5                   10

<210> SEQ ID NO 10
<211> LENGTH: 40
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 10

Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala Gly Ala Gly Ala
            20                  25                  30

Gly Ala Gly Ala Gly Ala Gly Ala
        35                  40

<210> SEQ ID NO 11
<211> LENGTH: 160
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 11

Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala Gly Ala Gly Ala
            20                  25                  30

Gly Ala Gly Ala Gly Ala Gly Ala Gly Ala Gly Ala Gly Ala Gly Ala
        35                  40                  45

Gly Ala Gly Ala Gly Ala Gly Ala Gly Ala Gly Ala Gly Ala Gly Ala
    50                  55                  60

Gly Ala Gly Ala Gly Ala Gly Ala Gly Ala Gly Ala Gly Ala Gly Ala
65                  70                  75                  80

Gly Ala Gly Ala Gly Ala Gly Ala Gly Ala Gly Ala Gly Ala Gly Ala
                85                  90                  95

Gly Ala Gly Ala Gly Ala Gly Ala Gly Ala Gly Ala Gly Ala Gly Ala
            100                 105                 110

Gly Ala Gly Ala Gly Ala Gly Ala Gly Ala Gly Ala Gly Ala Gly Ala
        115                 120                 125

Gly Ala Gly Ala Gly Ala Gly Ala Gly Ala Gly Ala Gly Ala Gly Ala
    130                 135                 140

Gly Ala Gly Ala Gly Ala Gly Ala Gly Ala Gly Ala Gly Ala Gly Ala
145                 150                 155                 160

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      auxiliary amino acid sequence
```

<400> SEQUENCE: 12

Gly Ala Gly Ala Gly Ser Gly Ala Gly Ala Gly Ser
1               5                   10

<210> SEQ ID NO 13
<211> LENGTH: 168
<212> TYPE: PRT
<213> ORGANISM: Artificial Sequence
<220> FEATURE:
<223> OTHER INFORMATION: Description of Artificial Sequence: Synthetic
      auxiliary amino acid sequence
<220> FEATURE:
<223> OTHER INFORMATION: This sequence may encompass 1-28 repeating
      "Gly Ala Gly Ala Gly Ser" units as defined in the specification

<400> SEQUENCE: 13

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Gly Ala Gly Ser Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser Gly Ala Gly Ala Gly Ser
            85                  90                  95

Gly Ala Gly Ala Gly Ser Gly Ala Gly Ala Gly Ser Gly Ala Gly Ala
                100                 105                 110

Gly Ser Gly Ala Gly Ala Gly Ser Gly Ala Gly Ala Gly Ser Gly Ala
            115                 120                 125

Gly Ala Gly Ser Gly Ala Gly Ala Gly Ser Gly Ala Gly Ala Gly Ser
        130                 135                 140

Gly Ala Gly Ala Gly Ser Gly Ala Gly Ala Gly Ser Gly Ala Gly Ala
145                 150                 155                 160

Gly Ser Gly Ala Gly Ala Gly Ser
                165

<210> SEQ ID NO 14
<211> LENGTH: 180
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 14

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Gly Ala Gly Ser Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser Gly Ala Gly Ala Gly Ser

```
                  85                  90                  95
Gly Ala Gly Ala Gly Ser Gly Ala Gly Ala Gly Ser Gly Ala Gly Ala
            100                 105                 110

Gly Ser Gly Ala Gly Ala Gly Ser Gly Ala Gly Ala Gly Ser Gly Ala
        115                 120                 125

Gly Ala Gly Ser Gly Ala Gly Ala Gly Ser Gly Ala Gly Ala Gly Ser
    130                 135                 140

Gly Ala Gly Ala Gly Ser Gly Ala Gly Ala Gly Ser Gly Ala Gly Ala
145                 150                 155                 160

Gly Ser Gly Ala Gly Ala Gly Ser Gly Ala Gly Ala Gly Ser Gly Ala
                165                 170                 175

Gly Ala Gly Ser
            180

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 15

Gly Ala Gly Ala Gly Tyr Gly Ala Gly Ala Gly Tyr
1               5                   10

<210> SEQ ID NO 16
<211> LENGTH: 54
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 16

Gly Ala Gly Ala Gly Tyr Gly Ala Gly Ala Gly Tyr Gly Ala Gly Ala
1               5                   10                  15

Gly Tyr Gly Ala Gly Ala Gly Tyr Gly Ala Gly Ala Gly Tyr Gly Ala
            20                  25                  30

Gly Ala Gly Tyr Gly Ala Gly Ala Gly Tyr Gly Ala Gly Ala Gly Tyr
        35                  40                  45

Gly Ala Gly Ala Gly Tyr
    50

<210> SEQ ID NO 17
<211> LENGTH: 180
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 17

Gly Ala Gly Ala Gly Tyr Gly Ala Gly Ala Gly Tyr Gly Ala Gly Ala
1               5                   10                  15

Gly Tyr Gly Ala Gly Ala Gly Tyr Gly Ala Gly Ala Gly Tyr Gly Ala
            20                  25                  30

Gly Ala Gly Tyr Gly Ala Gly Ala Gly Tyr Gly Ala Gly Ala Gly Tyr
        35                  40                  45

Gly Ala Gly Ala Gly Tyr Gly Ala Gly Ala Gly Tyr Gly Ala Gly Ala
    50                  55                  60
```

```
Gly Tyr Gly Ala Gly Ala Gly Tyr Gly Ala Gly Ala
 65                  70                  75                  80

Gly Ala Gly Tyr Gly Ala Gly Ala Gly Tyr Gly Ala Gly Ala Gly Tyr
             85                  90                  95

Gly Ala Gly Ala Gly Tyr Gly Ala Gly Ala Gly Tyr Gly Ala Gly Ala
        100                 105                 110

Gly Tyr Gly Ala Gly Ala Gly Tyr Gly Ala Gly Ala Gly Tyr Gly Ala
        115                 120                 125

Gly Ala Gly Tyr Gly Ala Gly Ala Gly Tyr Gly Ala Gly Ala Gly Tyr
        130                 135                 140

Gly Ala Gly Ala Gly Tyr Gly Ala Gly Ala Gly Tyr Gly Ala Gly Ala
145                 150                 155                 160

Gly Tyr Gly Ala Gly Ala Gly Tyr Gly Ala Gly Ala Gly Tyr Gly Ala
            165                 170                 175

Gly Ala Gly Tyr
        180

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 18

Gly Ala Gly Val Gly Tyr Gly Ala Gly Val Gly Tyr
1               5                   10

<210> SEQ ID NO 19
<211> LENGTH: 54
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 19

Gly Ala Gly Val Gly Tyr Gly Ala Gly Val Gly Tyr Gly Ala Gly Val
1               5                   10                  15

Gly Tyr Gly Ala Gly Val Gly Tyr Gly Ala Gly Val Gly Tyr Gly Ala
            20                  25                  30

Gly Val Gly Tyr Gly Ala Gly Val Gly Tyr Gly Ala Gly Val Gly Tyr
        35                  40                  45

Gly Ala Gly Val Gly Tyr
    50

<210> SEQ ID NO 20
<211> LENGTH: 180
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 20

Gly Ala Gly Val Gly Tyr Gly Ala Gly Val Gly Tyr Gly Ala Gly Val
1               5                   10                  15

Gly Tyr Gly Ala Gly Val Gly Tyr Gly Ala Gly Val Gly Tyr Gly Ala
            20                  25                  30

Gly Val Gly Tyr Gly Ala Gly Val Gly Tyr Gly Ala Gly Val Gly Tyr
        35                  40                  45
```

```
Gly Ala Gly Val Gly Tyr Gly Ala Gly Val Gly Tyr Gly Ala Gly Val
    50                  55                  60
Gly Tyr Gly Ala Gly Val Gly Tyr Gly Ala Gly Val Gly Tyr Gly Ala
65                  70                  75                  80
Gly Val Gly Tyr Gly Ala Gly Val Gly Tyr Gly Ala Gly Val Gly Tyr
                85                  90                  95
Gly Ala Gly Val Gly Tyr Gly Ala Gly Val Gly Tyr Gly Ala Gly Val
            100                 105                 110
Gly Tyr Gly Ala Gly Val Gly Tyr Gly Ala Gly Val Gly Tyr Gly Ala
        115                 120                 125
Gly Val Gly Tyr Gly Ala Gly Val Gly Tyr Gly Ala Gly Val Gly Tyr
    130                 135                 140
Gly Ala Gly Val Gly Tyr Gly Ala Gly Val Gly Tyr Gly Ala Gly Val
145                 150                 155                 160
Gly Tyr Gly Ala Gly Val Gly Tyr Gly Ala Gly Val Gly Tyr Gly Ala
                165                 170                 175
Gly Val Gly Tyr
            180

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 21

Gly Ala Gly Tyr Gly Val Gly Ala Gly Tyr Gly Val
1               5                   10

<210> SEQ ID NO 22
<211> LENGTH: 54
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 22

Gly Ala Gly Tyr Gly Val Gly Ala Gly Tyr Gly Val Gly Ala Gly Tyr
1               5                   10                  15
Gly Val Gly Ala Gly Tyr Gly Val Gly Ala Gly Tyr Gly Val Gly Ala
            20                  25                  30
Gly Tyr Gly Val Gly Ala Gly Tyr Gly Val Gly Ala Gly Tyr Gly Val
        35                  40                  45
Gly Ala Gly Tyr Gly Val
    50

<210> SEQ ID NO 23
<211> LENGTH: 180
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 23

Gly Ala Gly Tyr Gly Val Gly Ala Gly Tyr Gly Val Gly Ala Gly Tyr
1               5                   10                  15
Gly Val Gly Ala Gly Tyr Gly Val Gly Ala Gly Tyr Gly Val Gly Ala
```

```
                   20                  25                  30

Gly Tyr Gly Val Gly Ala Gly Tyr Gly Val Gly Ala Gly Tyr Gly Val
            35                  40                  45

Gly Ala Gly Tyr Gly Val Gly Ala Gly Tyr Gly Val Gly Ala Gly Tyr
        50                  55                  60

Gly Val Gly Ala Gly Tyr Gly Val Gly Ala Gly Tyr Gly Val Gly Ala
65                  70                  75                  80

Gly Tyr Gly Val Gly Ala Gly Tyr Gly Val Gly Ala Gly Tyr Gly Val
                85                  90                  95

Gly Ala Gly Tyr Gly Val Gly Ala Gly Tyr Gly Val Gly Ala Gly Tyr
            100                 105                 110

Gly Val Gly Ala Gly Tyr Gly Val Gly Ala Gly Tyr Gly Val Gly Ala
        115                 120                 125

Gly Tyr Gly Val Gly Ala Gly Tyr Gly Val Gly Ala Gly Tyr Gly Val
    130                 135                 140

Gly Ala Gly Tyr Gly Val Gly Ala Gly Tyr Gly Val Gly Ala Gly Tyr
145                 150                 155                 160

Gly Val Gly Ala Gly Tyr Gly Val Gly Ala Gly Tyr Gly Val Gly Ala
                165                 170                 175

Gly Tyr Gly Val
            180

<210> SEQ ID NO 24
<211> LENGTH: 48
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 24

Asp Gly Gly Ala Ala Ala Ala Ala Ala Gly Gly Ala Asp Gly Gly Ala
1               5                   10                  15

Ala Ala Ala Ala Ala Gly Gly Ala Asp Gly Gly Ala Ala Ala Ala Ala
            20                  25                  30

Ala Gly Gly Ala Asp Gly Gly Ala Ala Ala Ala Ala Ala Gly Gly Ala
        35                  40                  45

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 25

Asp Gly Gly Ala Ala Ala Ala Ala Ala Ala Ala Ala Ala Ala Ala Gly
1               5                   10                  15

Gly Ala

<210> SEQ ID NO 26
<211> LENGTH: 72
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 26

Asp Gly Gly Ala Ala Ala Ala Ala Ala Ala Ala Ala Ala Ala Ala Gly
```

```
                  1               5                  10                  15
Gly Ala Asp Gly Gly Ala Ala Ala Ala Ala Ala Ala Ala
                20                  25                  30

Ala Gly Gly Ala Asp Gly Gly Ala Ala Ala Ala Ala Ala
        35                  40                  45

Ala Ala Ala Gly Gly Ala Asp Gly Gly Ala Ala Ala Ala Ala
        50                  55                  60

Ala Ala Ala Ala Ala Gly Gly Ala
65                  70

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 27

Gly Val Pro Gly Val Gly Val Pro Gly Val
1               5                   10

<210> SEQ ID NO 28
<211> LENGTH: 50
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 28

Gly Val Pro Gly Val Gly Val Pro Gly Val Gly Val Pro Gly Val Gly
1               5                   10                  15

Val Pro Gly Val Gly Val Pro Gly Val Gly Val Pro Gly Val Gly Val
                20                  25                  30

Pro Gly Val Gly Val Pro Gly Val Gly Val Pro Gly Val Gly Val Pro
        35                  40                  45

Gly Val
    50

<210> SEQ ID NO 29
<211> LENGTH: 200
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 29

Gly Val Pro Gly Val Gly Val Pro Gly Val Gly Val Pro Gly Val Gly
1               5                   10                  15

Val Pro Gly Val Gly Val Pro Gly Val Gly Val Pro Gly Val Gly Val
                20                  25                  30

Pro Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
                85                  90                  95
```

```
Val Pro Gly Val Gly Val Pro Gly Val Gly Val
        100                 105                 110

Pro Gly Val Gly Val Pro Gly Val Gly Val Pro
        115                 120             125

Gly Val Gly Val Pro Gly Val Gly Val Pro Gly Val
    130                 135             140

Val Gly Val Pro Gly Val Gly Val Pro Gly Val Gly Val
145                 150                 155             160

Gly Val Pro Gly Val Gly Val Pro Gly Val Gly
            165                 170                 175

Val Pro Gly Val Gly Val Pro Gly Val Gly Val
        180                 185                 190

Pro Gly Val Gly Val Pro Gly Val
        195                 200

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 30

Gly Val Pro Gly Val Gly Val Pro Gly Val Gly Gly Ala Gly Ala
1               5                   10                  15

Gly Ser Gly Ala Gly Ala Gly Ser Gly Ala Gly Ala Gly Ser
            20                  25                  30

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 31

Gly Gly Gly Gly Gly Gly Gly Gly Gly Gly
1               5                   10

<210> SEQ ID NO 32
<211> LENGTH: 40
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 32

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

Gly Gly Gly Gly Gly Gly Gly Gly
        35                  40

<210> SEQ ID NO 33
<211> LENGTH: 160
<212> TYPE: PRT
<213> ORGANISM: Artificial Sequence
<220> FEATURE:
<223> OTHER INFORMATION: Description of Artificial Sequence: Synthetic
      auxiliary amino acid sequence
```

<400> SEQUENCE: 33

```
Gly Gly Gly Gly Gly Gly Gly Gly Gly Gly Gly Gly Gly Gly Gly Gly
1               5                   10                  15
Gly Gly Gly Gly Gly Gly Gly Gly Gly Gly Gly Gly Gly Gly Gly Gly
            20                  25                  30
Gly Gly Gly Gly Gly Gly Gly Gly Gly Gly Gly Gly Gly Gly Gly Gly
        35                  40                  45
Gly Gly Gly Gly Gly Gly Gly Gly Gly Gly Gly Gly Gly Gly Gly Gly
    50                  55                  60
Gly Gly Gly Gly Gly Gly Gly Gly Gly Gly Gly Gly Gly Gly Gly Gly
65                  70                  75                  80
Gly Gly Gly Gly Gly Gly Gly Gly Gly Gly Gly Gly Gly Gly Gly Gly
                85                  90                  95
Gly Gly Gly Gly Gly Gly Gly Gly Gly Gly Gly Gly Gly Gly Gly Gly
            100                 105                 110
Gly Gly Gly Gly Gly Gly Gly Gly Gly Gly Gly Gly Gly Gly Gly Gly
        115                 120                 125
Gly Gly Gly Gly Gly Gly Gly Gly Gly Gly Gly Gly Gly Gly Gly Gly
    130                 135                 140
Gly Gly Gly Gly Gly Gly Gly Gly Gly Gly Gly Gly Gly Gly Gly Gly
145                 150                 155                 160
```

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic auxiliary amino acid sequence

<400> SEQUENCE: 34

```
Ala Ala Ala Ala Ala Ala Ala Ala Ala Ala
1               5                   10
```

<210> SEQ ID NO 35
<211> LENGTH: 40
<212> TYPE: PRT
<213> ORGANISM: Artificial Sequence
<220> FEATURE:
<223> OTHER INFORMATION: Description of Artificial Sequence: Synthetic auxiliary amino acid sequence

<400> SEQUENCE: 35

```
Ala Ala Ala Ala Ala Ala Ala Ala Ala Ala Ala Ala Ala Ala Ala Ala
1               5                   10                  15
Ala Ala Ala Ala Ala Ala Ala Ala Ala Ala Ala Ala Ala Ala Ala Ala
            20                  25                  30
Ala Ala Ala Ala Ala Ala Ala Ala
        35                  40
```

<210> SEQ ID NO 36
<211> LENGTH: 160
<212> TYPE: PRT
<213> ORGANISM: Artificial Sequence
<220> FEATURE:
<223> OTHER INFORMATION: Description of Artificial Sequence: Synthetic auxiliary amino acid sequence

<400> SEQUENCE: 36

```
Ala Ala Ala Ala Ala Ala Ala Ala Ala Ala Ala Ala Ala Ala Ala Ala
1               5                   10                  15
```

Ala Ala Ala Ala Ala Ala Ala Ala Ala Ala Ala Ala
        20                  25                  30

Ala Ala Ala Ala Ala Ala Ala Ala Ala Ala Ala Ala
        35                  40                  45

Ala Ala Ala Ala Ala Ala Ala Ala Ala Ala Ala Ala
        50                  55                  60

Ala Ala Ala Ala Ala Ala Ala Ala Ala Ala Ala Ala
65                  70                  75                  80

Ala Ala Ala Ala Ala Ala Ala Ala Ala Ala Ala Ala
        85                  90                  95

Ala Ala Ala Ala Ala Ala Ala Ala Ala Ala Ala Ala
        100                 105                 110

Ala Ala Ala Ala Ala Ala Ala Ala Ala Ala Ala Ala
        115                 120                 125

Ala Ala Ala Ala Ala Ala Ala Ala Ala Ala Ala Ala
        130                 135                 140

Ala Ala Ala Ala Ala Ala Ala Ala Ala Ala Ala Ala
145                 150                 155                 160

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 37

Gly Gly Ala Gly Gly Ala Gly Gly Ala
1               5

<210> SEQ ID NO 38
<211> LENGTH: 36
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 38

Gly Gly Ala Gly Gly Ala Gly Gly Ala Gly Gly Ala Gly Gly Ala Gly
1               5                   10                  15

Gly Ala Gly Gly Ala Gly Gly Ala Gly Gly Ala Gly Gly Ala Gly Gly
        20                  25                  30

Ala Gly Gly Ala
        35

<210> SEQ ID NO 39
<211> LENGTH: 180
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 39

Gly Gly Ala Gly Gly Ala Gly Gly Ala Gly Gly Ala Gly Gly Ala Gly
1               5                   10                  15

Gly Ala Gly Gly Ala Gly Gly Ala Gly Gly Ala Gly Gly Ala Gly Gly
        20                  25                  30

Ala Gly Gly Ala Gly Gly Ala Gly Gly Ala Gly Gly Ala Gly Gly Ala

```
                    35                  40                  45
Gly Gly Ala Gly Gly Ala Gly Gly Ala Gly Gly Ala Gly Gly Ala Gly
     50                  55                  60
Gly Ala Gly Gly Ala Gly Gly Ala Gly Gly Ala Gly Gly Ala Gly Gly
 65                  70                  75                  80
Ala Gly Gly Ala Gly Gly Ala Gly Gly Ala Gly Gly Ala Gly Gly Ala
             85                  90                  95
Gly Gly Ala Gly Gly Ala Gly Gly Ala Gly Gly Ala Gly Gly Ala Gly
            100                 105                 110
Gly Ala Gly Gly Ala Gly Gly Ala Gly Gly Ala Gly Gly Ala Gly Gly
        115                 120                 125
Ala Gly Gly Ala Gly Gly Ala Gly Gly Ala Gly Gly Ala Gly Gly Ala
    130                 135                 140
Gly Gly Ala Gly Gly Ala Gly Gly Ala Gly Gly Ala Gly Gly Ala Gly
145                 150                 155                 160
Gly Ala Gly Gly Ala Gly Gly Ala Gly Gly Ala Gly Gly Ala Gly Gly
                165                 170                 175
Ala Gly Gly Ala
        180

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 40

Gly Val Gly Val Pro Gly Val Gly Val Pro
1               5                   10

<210> SEQ ID NO 41
<211> LENGTH: 50
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 41

Gly Val Gly Val Pro Gly Val Gly Val Pro Gly Val Gly Val Pro Gly
1               5                   10                  15
Val Gly Val Pro Gly Val Gly Val Pro Gly Val Gly Val Pro Gly Val
            20                  25                  30
Gly Val Pro Gly Val Gly Val Pro Gly Val Gly Val Pro Gly Val Gly
        35                  40                  45
Val Pro
    50

<210> SEQ ID NO 42
<211> LENGTH: 200
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 42

Gly Val Gly Val Pro Gly Val Gly Val Pro Gly Val Gly Val Pro Gly
1               5                   10                  15
```

```
Val Gly Val Pro Gly Val Gly Val Pro Gly Val
            20              25              30

Gly Val Pro Gly Val Gly Val Pro Gly Val Gly
            35              40              45

Val Pro Gly Val Gly Val Pro Gly Val Gly Val
    50              55              60

Pro Gly Val Gly Val Pro Gly Val Gly Val Pro
65              70              75          80

Gly Val Gly Val Pro Gly Val Gly Val Pro Gly
                85              90              95

Val Gly Val Pro Gly Val Gly Val Pro Gly Val
            100             105             110

Gly Val Pro Gly Val Gly Val Pro Gly Val Gly
            115             120             125

Val Pro Gly Val Gly Val Pro Gly Val Gly Val
    130             135             140

Pro Gly Val Gly Val Pro Gly Val Gly Val Pro
145             150             155         160

Gly Val Gly Val Pro Gly Val Gly Val Pro Gly
                165             170             175

Val Gly Val Pro Gly Val Gly Val Pro Gly Val
            180             185             190

Gly Val Pro Gly Val Gly Val Pro
        195             200

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 43

Gly Pro Pro Gly Pro Pro Gly Pro Pro
1               5

<210> SEQ ID NO 44
<211> LENGTH: 36
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 44

Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro Gly Pro
            20                  25                  30

Pro Gly Pro Pro
        35

<210> SEQ ID NO 45
<211> LENGTH: 180
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 45
```

Gly Pro Pro Gly Pro Pro Gly Pro Pro Gly Pro Pro Gly
1               5                   10                  15

Pro Pro Gly Pro Pro Gly Pro Pro Gly Pro Pro Gly Pro
                20                  25                  30

Pro Gly Pro Pro Gly Pro Pro Gly Pro Pro Gly Pro Pro
        35                  40                  45

Gly Pro Pro Gly Pro Pro Gly Pro Pro Gly Pro Pro Gly
    50                  55                  60

Pro Pro Gly Pro Pro Gly Pro Pro Gly Pro Pro Gly Pro
65              70                  75                  80

Pro Gly Pro Pro Gly Pro Pro Gly Pro Pro Gly Pro Pro
        85                  90                  95

Gly Pro Pro Gly Pro Pro Gly Pro Pro Gly Pro Pro Gly
        100                 105                 110

Pro Pro Gly Pro Pro Gly Pro Pro Gly Pro Pro Gly Pro
        115                 120                 125

Pro Gly Pro Pro Gly Pro Pro Gly Pro Pro Gly Pro Pro
    130                 135                 140

Gly Pro Pro Gly Pro Pro Gly Pro Pro Gly Pro Pro Gly
145             150                 155                 160

Pro Pro Gly Pro Pro Gly Pro Pro Gly Pro Pro Gly Pro
            165                 170                 175

Pro Gly Pro Pro
        180

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 46

Gly Ala Gln Gly Pro Ala Gly Pro Gly
1               5

<210> SEQ ID NO 47
<211> LENGTH: 45
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 47

Gly Ala Gln Gly Pro Ala Gly Pro Gly Gly Ala Gln Gly Pro Ala Gly
1               5                   10                  15

Pro Gly Gly Ala Gln Gly Pro Ala Gly Pro Gly Gly Ala Gln Gly Pro
                20                  25                  30

Ala Gly Pro Gly Gly Ala Gln Gly Pro Ala Gly Pro Gly
        35                  40                  45

<210> SEQ ID NO 48
<211> LENGTH: 180
<212> TYPE: PRT
<213> ORGANISM: Artificial Sequence
<220> FEATURE:
<223> OTHER INFORMATION: Description of Artificial Sequence: Synthetic
      auxiliary amino acid sequence -continued

<400> SEQUENCE: 48

Gly Ala Gln Gly Pro Ala Gly Pro Gly Gly Ala Gln Gly Pro Ala Gly
1               5                   10                  15

Pro Gly Gly Ala Gln Gly Pro Ala Gly Pro Gly Gly Ala Gln Gly Pro
                20                  25                  30

Ala Gly Pro Gly Gly Ala Gln Gly Pro Ala Gly Pro Gly Gly Ala Gln
            35                  40                  45

Gly Pro Ala Gly Pro Gly Gly Ala Gln Gly Pro Ala Gly Pro Gly Gly
        50                  55                  60

Ala Gln Gly Pro Ala Gly Pro Gly Gly Ala Gln Gly Pro Ala Gly Pro
65                  70                  75                  80

Gly Gly Ala Gln Gly Pro Ala Gly Pro Gly Gly Ala Gln Gly Pro Ala
                85                  90                  95

Gly Pro Gly Gly Ala Gln Gly Pro Ala Gly Pro Gly Gly Ala Gln Gly
            100                 105                 110

Pro Ala Gly Pro Gly Gly Ala Gln Gly Pro Ala Gly Pro Gly Gly Ala
        115                 120                 125

Gln Gly Pro Ala Gly Pro Gly Gly Ala Gln Gly Pro Ala Gly Pro Gly
    130                 135                 140

Gly Ala Gln Gly Pro Ala Gly Pro Gly Gly Ala Gln Gly Pro Ala Gly
145                 150                 155                 160

Pro Gly Gly Ala Gln Gly Pro Ala Gly Pro Gly Gly Ala Gln Gly Pro
                165                 170                 175

Ala Gly Pro Gly
            180

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 49

Gly Ala Pro Gly Ala Pro Gly Ser Gln Gly Ala Pro Gly Leu Gln
1               5                   10                  15

<210> SEQ ID NO 50
<211> LENGTH: 60
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 50

Gly Ala Pro Gly Ala Pro Gly Ser Gln Gly Ala Pro Gly Leu Gln Gly
1               5                   10                  15

Ala Pro Gly Ala Pro Gly Ser Gln Gly Ala Pro Gly Leu Gln Gly Ala
                20                  25                  30

Pro Gly Ala Pro Gly Ser Gln Gly Ala Pro Gly Leu Gln Gly Ala Pro
            35                  40                  45

Gly Ala Pro Gly Ser Gln Gly Ala Pro Gly Leu Gln
        50                  55                  60

<210> SEQ ID NO 51
<211> LENGTH: 180
<212> TYPE: PRT
<213> ORGANISM: Artificial Sequence -continued
<220> FEATURE:
<223> OTHER INFORMATION: Description of Artificial Sequence: Synthetic
      auxiliary amino acid sequence

<400> SEQUENCE: 51

Gly Ala Pro Gly Ala Pro Gly Ser Gln Gly Ala Pro Gly Leu Gln Gly
1               5                   10                  15

Ala Pro Gly Ala Pro Gly Ser Gln Gly Ala Pro Gly Leu Gln Gly Ala
            20                  25                  30

Pro Gly Ala Pro Gly Ser Gln Gly Ala Pro Gly Leu Gln Gly Ala Pro
        35                  40                  45

Gly Ala Pro Gly Ser Gln Gly Ala Pro Gly Leu Gln Gly Ala Pro Gly
50                  55                  60

Ala Pro Gly Ser Gln Gly Ala Pro Gly Leu Gln Gly Ala Pro Gly Ala
65                  70                  75                  80

Pro Gly Ser Gln Gly Ala Pro Gly Leu Gln Gly Ala Pro Gly Ala Pro
                85                  90                  95

Gly Ser Gln Gly Ala Pro Gly Leu Gln Gly Ala Pro Gly Ala Pro Gly
            100                 105                 110

Ser Gln Gly Ala Pro Gly Leu Gln Gly Ala Pro Gly Ala Pro Gly Ser
        115                 120                 125

Gln Gly Ala Pro Gly Leu Gln Gly Ala Pro Gly Ala Pro Gly Ser Gln
130                 135                 140

Gly Ala Pro Gly Leu Gln Gly Ala Pro Gly Ala Pro Gly Ser Gln Gly
145                 150                 155                 160

Ala Pro Gly Leu Gln Gly Ala Pro Gly Ala Pro Gly Ser Gln Gly Ala
                165                 170                 175

Pro Gly Leu Gln
            180

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 52

Gly Ala Pro Gly Thr Pro Gly Pro Gln Gly Leu Pro Gly Ser Pro
1               5                   10                  15

<210> SEQ ID NO 53
<211> LENGTH: 60
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 53

Gly Ala Pro Gly Thr Pro Gly Pro Gln Gly Leu Pro Gly Ser Pro Gly
1               5                   10                  15

Ala Pro Gly Thr Pro Gly Pro Gln Gly Leu Pro Gly Ser Pro Gly Ala
            20                  25                  30

Pro Gly Thr Pro Gly Pro Gln Gly Leu Pro Gly Ser Pro Gly Ala Pro
        35                  40                  45

Gly Thr Pro Gly Pro Gln Gly Leu Pro Gly Ser Pro
50                  55                  60

```
<210> SEQ ID NO 54
<211> LENGTH: 180
<212> TYPE: PRT
<213> ORGANISM: Artificial Sequence
<220> FEATURE:
<223> OTHER INFORMATION: Description of Artificial Sequence: Synthetic
      auxiliary amino acid sequence

<400> SEQUENCE: 54

Gly Ala Pro Gly Thr Pro Gly Pro Gln Gly Leu Pro Gly Ser Pro Gly
1               5                   10                  15

Ala Pro Gly Thr Pro Gly Pro Gln Gly Leu Pro Gly Ser Pro Gly Ala
                20                  25                  30

Pro Gly Thr Pro Gly Pro Gln Gly Leu Pro Gly Ser Pro Gly Ala Pro
            35                  40                  45

Gly Thr Pro Gly Pro Gln Gly Leu Pro Gly Ser Pro Gly Ala Pro Gly
        50                  55                  60

Thr Pro Gly Pro Gln Gly Leu Pro Gly Ser Pro Gly Ala Pro Gly Thr
65                  70                  75                  80

Pro Gly Pro Gln Gly Leu Pro Gly Ser Pro Gly Ala Pro Gly Thr Pro
                85                  90                  95

Gly Pro Gln Gly Leu Pro Gly Ser Pro Gly Ala Pro Gly Thr Pro Gly
                100                 105                 110

Pro Gln Gly Leu Pro Gly Ser Pro Gly Ala Pro Gly Thr Pro Gly Pro
            115                 120                 125

Gln Gly Leu Pro Gly Ser Pro Gly Ala Pro Gly Thr Pro Gly Pro Gln
130                 135                 140

Gly Leu Pro Gly Ser Pro Gly Ala Pro Gly Thr Pro Gly Pro Gln Gly
145                 150                 155                 160

Leu Pro Gly Ser Pro Gly Ala Pro Gly Thr Pro Gly Pro Gln Gly Leu
                165                 170                 175

Pro Gly Ser Pro
            180

<210> SEQ ID NO 55
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 5-100 "Gly Ala"
      repeating units

<400> SEQUENCE: 55

Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala Gly Ala Gly Ala
                20                  25                  30

Gly Ala Gly Ala Gly Ala Gly Ala Gly Ala Gly Ala Gly Ala Gly Ala
            35                  40                  45

Gly Ala Gly Ala Gly Ala Gly Ala Gly Ala Gly Ala Gly Ala Gly Ala
        50                  55                  60

Gly Ala Gly Ala Gly Ala Gly Ala Gly Ala Gly Ala Gly Ala Gly Ala
65                  70                  75                  80

Gly Ala Gly Ala Gly Ala Gly Ala Gly Ala Gly Ala Gly Ala Gly Ala
                85                  90                  95

Gly Ala Gly Ala Gly Ala Gly Ala Gly Ala Gly Ala Gly Ala Gly Ala
                100                 105                 110
```

```
Gly Ala Gly Ala Gly Ala Gly Ala Gly Ala Gly Ala Gly Ala Gly Ala
        115                 120                 125

Gly Ala Gly Ala Gly Ala Gly Ala Gly Ala Gly Ala Gly Ala Gly Ala
    130                 135                 140

Gly Ala Gly Ala Gly Ala Gly Ala Gly Ala Gly Ala Gly Ala Gly Ala
145                 150                 155                 160

Gly Ala Gly Ala Gly Ala Gly Ala Gly Ala Gly Ala Gly Ala Gly Ala
        165                 170                 175

Gly Ala Gly Ala Gly Ala Gly Ala Gly Ala Gly Ala Gly Ala Gly Ala
    180                 185                 190

Gly Ala Gly Ala Gly Ala Gly Ala
        195                 200

<210> SEQ ID NO 56
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 2-33 "Gly Ala Gly
      Ala Gly Ser" repeating units

<400> SEQUENCE: 56

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Gly Ala Gly Ser Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser Gly Ala Gly Ala Gly Ser
            85                  90                  95

Gly Ala Gly Ala Gly Ser Gly Ala Gly Ala Gly Ser Gly Ala Gly Ala
        100                 105                 110

Gly Ser Gly Ala Gly Ala Gly Ser Gly Ala Gly Ala Gly Ser Gly Ala
    115                 120                 125

Gly Ala Gly Ser Gly Ala Gly Ala Gly Ser Gly Ala Gly Ala Gly Ser
    130                 135                 140

Gly Ala Gly Ala Gly Ser Gly Ala Gly Ala Gly Ser Gly Ala Gly Ala
145                 150                 155                 160

Gly Ser Gly Ala Gly Ala Gly Ser Gly Ala Gly Ala Gly Ser Gly Ala
            165                 170                 175

Gly Ala Gly Ser Gly Ala Gly Ala Gly Ser Gly Ala Gly Ala Gly Ser
        180                 185                 190

Gly Ala Gly Ala Gly Ser
        195

<210> SEQ ID NO 57
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: This sequence may encompass 2-33 "Gly Ala Gly
      Ala Gly Tyr" repeating units

<400> SEQUENCE: 57

Gly Ala Gly Ala Gly Tyr Gly Ala Gly Ala Gly Tyr Gly Ala Gly Ala
1               5                   10                  15

Gly Tyr Gly Ala Gly Ala Gly Tyr Gly Ala Gly Ala Gly Tyr Gly Ala
            20                  25                  30

Gly Ala Gly Tyr Gly Ala Gly Ala Gly Tyr Gly Ala Gly Ala Gly Tyr
        35                  40                  45

Gly Ala Gly Ala Gly Tyr Gly Ala Gly Ala Gly Tyr Gly Ala Gly Ala
50                  55                  60

Gly Tyr Gly Ala Gly Ala Gly Tyr Gly Ala Gly Ala Gly Tyr Gly Ala
65                  70                  75                  80

Gly Ala Gly Tyr Gly Ala Gly Ala Gly Tyr Gly Ala Gly Ala Gly Tyr
            85                  90                  95

Gly Ala Gly Ala Gly Tyr Gly Ala Gly Ala Gly Tyr Gly Ala Gly Ala
            100                 105                 110

Gly Tyr Gly Ala Gly Ala Gly Tyr Gly Ala Gly Ala Gly Tyr Gly Ala
        115                 120                 125

Gly Ala Gly Tyr Gly Ala Gly Ala Gly Tyr Gly Ala Gly Ala Gly Tyr
        130                 135                 140

Gly Ala Gly Ala Gly Tyr Gly Ala Gly Ala Gly Tyr Gly Ala Gly Ala
145                 150                 155                 160

Gly Tyr Gly Ala Gly Ala Gly Tyr Gly Ala Gly Ala Gly Tyr Gly Ala
            165                 170                 175

Gly Ala Gly Tyr Gly Ala Gly Ala Gly Tyr Gly Ala Gly Ala Gly Tyr
            180                 185                 190

Gly Ala Gly Ala Gly Tyr
            195

<210> SEQ ID NO 58
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 2-33 "Gly Ala Gly
      Val Gly Tyr" repeating units

<400> SEQUENCE: 58

Gly Ala Gly Val Gly Tyr Gly Ala Gly Val Gly Tyr Gly Ala Gly Val
1               5                   10                  15

Gly Tyr Gly Ala Gly Val Gly Tyr Gly Ala Gly Val Gly Tyr Gly Ala
            20                  25                  30

Gly Val Gly Tyr Gly Ala Gly Val Gly Tyr Gly Ala Gly Val Gly Tyr
        35                  40                  45

Gly Ala Gly Val Gly Tyr Gly Ala Gly Val Gly Tyr Gly Ala Gly Val
50                  55                  60

Gly Tyr Gly Ala Gly Val Gly Tyr Gly Ala Gly Val Gly Tyr Gly Ala
65                  70                  75                  80

Gly Val Gly Tyr Gly Ala Gly Val Gly Tyr Gly Ala Gly Val Gly Tyr
            85                  90                  95

Gly Ala Gly Val Gly Tyr Gly Ala Gly Val Gly Tyr Gly Ala Gly Val
            100                 105                 110
```

Gly Tyr Gly Ala Gly Val Gly Tyr Gly Ala Gly Val Gly Tyr Gly Ala
            115                 120                 125

Gly Val Gly Tyr Gly Ala Gly Val Gly Tyr Gly Ala Gly Val Gly Tyr
        130                 135                 140

Gly Ala Gly Val Gly Tyr Gly Ala Gly Val Gly Tyr Gly Ala Gly Val
145                 150                 155                 160

Gly Tyr Gly Ala Gly Val Gly Tyr Gly Ala Gly Val Gly Tyr Gly Ala
            165                 170                 175

Gly Val Gly Tyr Gly Ala Gly Val Gly Tyr Gly Ala Gly Val Gly Tyr
        180                 185                 190

Gly Ala Gly Val Gly Tyr
        195

<210> SEQ ID NO 59
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 2-33 "Gly Ala Gly
      Tyr Gly Val" repeating units

<400> SEQUENCE: 59

Gly Ala Gly Tyr Gly Val Gly Ala Gly Tyr Gly Val Gly Ala Gly Tyr
1               5                   10                  15

Gly Val Gly Ala Gly Tyr Gly Val Gly Ala Gly Tyr Gly Val Gly Ala
            20                  25                  30

Gly Tyr Gly Val Gly Ala Gly Tyr Gly Val Gly Ala Gly Tyr Gly Val
        35                  40                  45

Gly Ala Gly Tyr Gly Val Gly Ala Gly Tyr Gly Val Gly Ala Gly Tyr
50                  55                  60

Gly Val Gly Ala Gly Tyr Gly Val Gly Ala Gly Tyr Gly Val Gly Ala
65                  70                  75                  80

Gly Tyr Gly Val Gly Ala Gly Tyr Gly Val Gly Ala Gly Tyr Gly Val
            85                  90                  95

Gly Ala Gly Tyr Gly Val Gly Ala Gly Tyr Gly Val Gly Ala Gly Tyr
        100                 105                 110

Gly Val Gly Ala Gly Tyr Gly Val Gly Ala Gly Tyr Gly Val Gly Ala
            115                 120                 125

Gly Tyr Gly Val Gly Ala Gly Tyr Gly Val Gly Ala Gly Tyr Gly Val
        130                 135                 140

Gly Ala Gly Tyr Gly Val Gly Ala Gly Tyr Gly Val Gly Ala Gly Tyr
145                 150                 155                 160

Gly Val Gly Ala Gly Tyr Gly Val Gly Ala Gly Tyr Gly Val Gly Ala
            165                 170                 175

Gly Tyr Gly Val Gly Ala Gly Tyr Gly Val Gly Ala Gly Tyr Gly Val
        180                 185                 190

Gly Ala Gly Tyr Gly Val
        195

<210> SEQ ID NO 60
<211> LENGTH: 5600
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

```
<221> NAME/KEY: MOD_RES
<222> LOCATION: (4)..(197)
<223> OTHER INFORMATION: This region may encompass 1-194 Ala residues
<220> FEATURE:
<221> NAME/KEY: MOD_RES
<222> LOCATION: (204)..(397)
<223> OTHER INFORMATION: This region may encompass 1-194 Ala residues
<220> FEATURE:
<221> NAME/KEY: MOD_RES
<222> LOCATION: (404)..(597)
<223> OTHER INFORMATION: This region may encompass 1-194 Ala residues
<220> FEATURE:
<221> NAME/KEY: MOD_RES
<222> LOCATION: (604)..(797)
<223> OTHER INFORMATION: This region may encompass 1-194 Ala residues
<220> FEATURE:
<221> NAME/KEY: MOD_RES
<222> LOCATION: (804)..(997)
<223> OTHER INFORMATION: This region may encompass 1-194 Ala residues
<220> FEATURE:
<221> NAME/KEY: MOD_RES
<222> LOCATION: (1004)..(1197)
<223> OTHER INFORMATION: This region may encompass 1-194 Ala residues
<220> FEATURE:
<221> NAME/KEY: MOD_RES
<222> LOCATION: (1204)..(1397)
<223> OTHER INFORMATION: This region may encompass 1-194 Ala residues
<220> FEATURE:
<221> NAME/KEY: MOD_RES
<222> LOCATION: (1404)..(1597)
<223> OTHER INFORMATION: This region may encompass 1-194 Ala residues
<220> FEATURE:
<221> NAME/KEY: MOD_RES
<222> LOCATION: (1604)..(1797)
<223> OTHER INFORMATION: This region may encompass 1-194 Ala residues
<220> FEATURE:
<221> NAME/KEY: MOD_RES
<222> LOCATION: (1804)..(1997)
<223> OTHER INFORMATION: This region may encompass 1-194 Ala residues
<220> FEATURE:
<221> NAME/KEY: MOD_RES
<222> LOCATION: (2004)..(2197)
<223> OTHER INFORMATION: This region may encompass 1-194 Ala residues
<220> FEATURE:
<221> NAME/KEY: MOD_RES
<222> LOCATION: (2204)..(2397)
<223> OTHER INFORMATION: This region may encompass 1-194 Ala residues
<220> FEATURE:
<221> NAME/KEY: MOD_RES
<222> LOCATION: (2404)..(2597)
<223> OTHER INFORMATION: This region may encompass 1-194 Ala residues
<220> FEATURE:
<221> NAME/KEY: MOD_RES
<222> LOCATION: (2604)..(2797)
<223> OTHER INFORMATION: This region may encompass 1-194 Ala residues
<220> FEATURE:
<221> NAME/KEY: MOD_RES
<222> LOCATION: (2804)..(2997)
<223> OTHER INFORMATION: This region may encompass 1-194 Ala residues
<220> FEATURE:
<221> NAME/KEY: MOD_RES
<222> LOCATION: (3004)..(3197)
<223> OTHER INFORMATION: This region may encompass 1-194 Ala residues
<220> FEATURE:
<221> NAME/KEY: MOD_RES
<222> LOCATION: (3204)..(3397)
<223> OTHER INFORMATION: This region may encompass 1-194 Ala residues
<220> FEATURE:
<221> NAME/KEY: MOD_RES
<222> LOCATION: (3404)..(3597)
<223> OTHER INFORMATION: This region may encompass 1-194 Ala residues
<220> FEATURE:
<221> NAME/KEY: MOD_RES
<222> LOCATION: (3604)..(3797)
<223> OTHER INFORMATION: This region may encompass 1-194 Ala residues
<220> FEATURE:
<221> NAME/KEY: MOD_RES
<222> LOCATION: (3804)..(3997)
<223> OTHER INFORMATION: This region may encompass 1-194 Ala residues
<220> FEATURE:
```

```
<221> NAME/KEY: MOD_RES
<222> LOCATION: (4004)..(4197)
<223> OTHER INFORMATION: This region may encompass 1-194 Ala residues
<220> FEATURE:
<221> NAME/KEY: MOD_RES
<222> LOCATION: (4204)..(4397)
<223> OTHER INFORMATION: This region may encompass 1-194 Ala residues
<220> FEATURE:
<221> NAME/KEY: MOD_RES
<222> LOCATION: (4404)..(4597)
<223> OTHER INFORMATION: This region may encompass 1-194 Ala residues
<220> FEATURE:
<221> NAME/KEY: MOD_RES
<222> LOCATION: (4604)..(4797)
<223> OTHER INFORMATION: This region may encompass 1-194 Ala residues
<220> FEATURE:
<221> NAME/KEY: MOD_RES
<222> LOCATION: (4804)..(4997)
<223> OTHER INFORMATION: This region may encompass 1-194 Ala residues
<220> FEATURE:
<221> NAME/KEY: MOD_RES
<222> LOCATION: (5004)..(5197)
<223> OTHER INFORMATION: This region may encompass 1-194 Ala residues
<220> FEATURE:
<221> NAME/KEY: MOD_RES
<222> LOCATION: (5204)..(5397)
<223> OTHER INFORMATION: This region may encompass 1-194 Ala residues
<220> FEATURE:
<221> NAME/KEY: MOD_RES
<222> LOCATION: (5404)..(5597)
<223> OTHER INFORMATION: This region may encompass 1-194 Ala residues
<220> FEATURE:
<223> OTHER INFORMATION: This sequence may encompass 1-28 repeating
      7-200 residue units as defined in the specification

<400> SEQUENCE: 60

Asp Gly Gly Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala Ala Ala Ala Ala Ala Ala Ala Ala Ala Ala Ala Ala
        35                  40                  45

Ala Ala Ala Ala Ala Ala Ala Ala Ala Ala Ala Ala Ala Ala Ala Ala
    50                  55                  60

Ala Ala Ala Ala Ala Ala Ala Ala Ala Ala Ala Ala Ala Ala Ala Ala
65                  70                  75                  80

Ala Ala Ala Ala Ala Ala Ala Ala Ala Ala Ala Ala Ala Ala Ala Ala
                85                  90                  95

Ala Ala Ala Ala Ala Ala Ala Ala Ala Ala Ala Ala Ala Ala Ala Ala
            100                 105                 110

Ala Ala Ala Ala Ala Ala Ala Ala Ala Ala Ala Ala Ala Ala Ala Ala
        115                 120                 125

Ala Ala Ala Ala Ala Ala Ala Ala Ala Ala Ala Ala Ala Ala Ala Ala
    130                 135                 140

Ala Ala Ala Ala Ala Ala Ala Ala Ala Ala Ala Ala Ala Ala Ala Ala
145                 150                 155                 160

Ala Ala Ala Ala Ala Ala Ala Ala Ala Ala Ala Ala Ala Ala Ala Ala
                165                 170                 175

Ala Ala Ala Ala Ala Ala Ala Ala Ala Ala Ala Ala Ala Ala Ala Ala
            180                 185                 190

Ala Ala Ala Ala Ala Gly Gly Ala Asp Gly Gly Ala Ala Ala Ala Ala
        195                 200                 205

Ala Ala Ala Ala Ala Ala Ala Ala Ala Ala Ala Ala Ala Ala Ala Ala
    210                 215                 220

Ala Ala Ala Ala Ala Ala Ala Ala Ala Ala Ala Ala Ala Ala Ala Ala
```

225                 230                 235                 240

Ala Ala Ala Ala Ala Ala Ala Ala Ala Ala Ala Ala Ala Ala Ala
                245                 250                 255

Ala Ala Ala Ala Ala Ala Ala Ala Ala Ala Ala Ala Ala Ala Ala
                260                 265                 270

Ala Ala Ala Ala Ala Ala Ala Ala Ala Ala Ala Ala Ala Ala Ala
                275                 280                 285

Ala Ala Ala Ala Ala Ala Ala Ala Ala Ala Ala Ala Ala Ala Ala
                290                 295                 300

Ala Ala Ala Ala Ala Ala Ala Ala Ala Ala Ala Ala Ala Ala Ala
305                 310                 315                 320

Ala Ala Ala Ala Ala Ala Ala Ala Ala Ala Ala Ala Ala Ala Ala
                325                 330                 335

Ala Ala Ala Ala Ala Ala Ala Ala Ala Ala Ala Ala Ala Ala Ala
                340                 345                 350

Ala Ala Ala Ala Ala Ala Ala Ala Ala Ala Ala Ala Ala Ala Ala
                355                 360                 365

Ala Ala Ala Ala Ala Ala Ala Ala Ala Ala Ala Ala Ala Ala Ala
                370                 375                 380

Ala Ala Ala Ala Ala Ala Ala Ala Ala Ala Ala Ala Ala Gly Gly Ala
385                 390                 395                 400

Asp Gly Gly Ala Ala Ala Ala Ala Ala Ala Ala Ala Ala Ala Ala
                405                 410                 415

Ala Ala Ala Ala Ala Ala Ala Ala Ala Ala Ala Ala Ala Ala Ala
                420                 425                 430

Ala Ala Ala Ala Ala Ala Ala Ala Ala Ala Ala Ala Ala Ala Ala
                435                 440                 445

Ala Ala Ala Ala Ala Ala Ala Ala Ala Ala Ala Ala Ala Ala Ala
                450                 455                 460

Ala Ala Ala Ala Ala Ala Ala Ala Ala Ala Ala Ala Ala Ala Ala
465                 470                 475                 480

Ala Ala Ala Ala Ala Ala Ala Ala Ala Ala Ala Ala Ala Ala Ala
                485                 490                 495

Ala Ala Ala Ala Ala Ala Ala Ala Ala Ala Ala Ala Ala Ala Ala
                500                 505                 510

Ala Ala Ala Ala Ala Ala Ala Ala Ala Ala Ala Ala Ala Ala Ala
                515                 520                 525

Ala Ala Ala Ala Ala Ala Ala Ala Ala Ala Ala Ala Ala Ala Ala
                530                 535                 540

Ala Ala Ala Ala Ala Ala Ala Ala Ala Ala Ala Ala Ala Ala Ala
545                 550                 555                 560

Ala Ala Ala Ala Ala Ala Ala Ala Ala Ala Ala Ala Ala Ala Ala
                565                 570                 575

Ala Ala Ala Ala Ala Ala Ala Ala Ala Ala Ala Ala Ala Ala Ala
                580                 585                 590

Ala Ala Ala Ala Ala Gly Gly Ala Asp Gly Gly Ala Ala Ala Ala
                595                 600                 605

Ala Ala Ala Ala Ala Ala Ala Ala Ala Ala Ala Ala Ala Ala Ala
                610                 615                 620

Ala Ala Ala Ala Ala Ala Ala Ala Ala Ala Ala Ala Ala Ala Ala
625                 630                 635                 640

Ala Ala Ala Ala Ala Ala Ala Ala Ala Ala Ala Ala Ala Ala Ala
                645                 650                 655

-continued

Ala Ala Ala Ala Ala Ala Ala Ala Ala Ala Ala Ala
                660             665             670

Ala Ala Ala Ala Ala Ala Ala Ala Ala Ala Ala Ala
        675             680             685

Ala Ala Ala Ala Ala Ala Ala Ala Ala Ala Ala Ala
690             695             700

Ala Ala Ala Ala Ala Ala Ala Ala Ala Ala Ala Ala
705             710             715             720

Ala Ala Ala Ala Ala Ala Ala Ala Ala Ala Ala Ala
            725             730             735

Ala Ala Ala Ala Ala Ala Ala Ala Ala Ala Ala Ala
        740             745             750

Ala Ala Ala Ala Ala Ala Ala Ala Ala Ala Ala Ala
    755             760             765

Ala Ala Ala Ala Ala Ala Ala Ala Ala Ala Ala Ala
770             775             780

Ala Ala Ala Ala Ala Ala Ala Ala Ala Gly Gly Ala
785             790             795             800

Asp Gly Gly Ala Ala Ala Ala Ala Ala Ala Ala Ala
            805             810             815

Ala Ala Ala Ala Ala Ala Ala Ala Ala Ala Ala Ala
        820             825             830

Ala Ala Ala Ala Ala Ala Ala Ala Ala Ala Ala Ala
    835             840             845

Ala Ala Ala Ala Ala Ala Ala Ala Ala Ala Ala Ala
850             855             860

Ala Ala Ala Ala Ala Ala Ala Ala Ala Ala Ala Ala
865             870             875             880

Ala Ala Ala Ala Ala Ala Ala Ala Ala Ala Ala Ala
            885             890             895

Ala Ala Ala Ala Ala Ala Ala Ala Ala Ala Ala Ala
        900             905             910

Ala Ala Ala Ala Ala Ala Ala Ala Ala Ala Ala Ala
    915             920             925

Ala Ala Ala Ala Ala Ala Ala Ala Ala Ala Ala Ala
930             935             940

Ala Ala Ala Ala Ala Ala Ala Ala Ala Ala Ala Ala
945             950             955             960

Ala Ala Ala Ala Ala Ala Ala Ala Ala Ala Ala Ala
            965             970             975

Ala Ala Ala Ala Ala Ala Ala Ala Ala Ala Ala Ala
        980             985             990

Ala Ala Ala Ala Ala Gly Gly Ala Asp Gly Gly Ala Ala Ala Ala Ala
    995             1000            1005

Ala Ala Ala Ala Ala Ala Ala Ala Ala Ala Ala Ala Ala Ala
    1010            1015            1020

Ala Ala Ala Ala Ala Ala Ala Ala Ala Ala Ala Ala Ala Ala
    1025            1030            1035

Ala Ala Ala Ala Ala Ala Ala Ala Ala Ala Ala Ala Ala Ala
    1040            1045            1050

Ala Ala Ala Ala Ala Ala Ala Ala Ala Ala Ala Ala Ala Ala
    1055            1060            1065

Ala Ala Ala Ala Ala Ala Ala Ala Ala Ala Ala Ala Ala Ala
    1070            1075            1080

-continued

Ala Ala Ala Ala Ala Ala Ala Ala Ala Ala Ala Ala Ala Ala
    1085                1090                1095

Ala Ala Ala Ala Ala Ala Ala Ala Ala Ala Ala Ala Ala Ala
    1100                1105                1110

Ala Ala Ala Ala Ala Ala Ala Ala Ala Ala Ala Ala Ala Ala
    1115                1120                1125

Ala Ala Ala Ala Ala Ala Ala Ala Ala Ala Ala Ala Ala Ala
    1130                1135                1140

Ala Ala Ala Ala Ala Ala Ala Ala Ala Ala Ala Ala Ala Ala
    1145                1150                1155

Ala Ala Ala Ala Ala Ala Ala Ala Ala Ala Ala Ala Ala Ala
    1160                1165                1170

Ala Ala Ala Ala Ala Ala Ala Ala Ala Ala Ala Ala Ala Ala
    1175                1180                1185

Ala Ala Ala Ala Ala Ala Ala Ala Gly Gly Ala Asp Gly Gly
    1190                1195                1200

Ala Ala Ala Ala Ala Ala Ala Ala Ala Ala Ala Ala Ala Ala
    1205                1210                1215

Ala Ala Ala Ala Ala Ala Ala Ala Ala Ala Ala Ala Ala Ala
    1220                1225                1230

Ala Ala Ala Ala Ala Ala Ala Ala Ala Ala Ala Ala Ala Ala
    1235                1240                1245

Ala Ala Ala Ala Ala Ala Ala Ala Ala Ala Ala Ala Ala Ala
    1250                1255                1260

Ala Ala Ala Ala Ala Ala Ala Ala Ala Ala Ala Ala Ala Ala
    1265                1270                1275

Ala Ala Ala Ala Ala Ala Ala Ala Ala Ala Ala Ala Ala Ala
    1280                1285                1290

Ala Ala Ala Ala Ala Ala Ala Ala Ala Ala Ala Ala Ala Ala
    1295                1300                1305

Ala Ala Ala Ala Ala Ala Ala Ala Ala Ala Ala Ala Ala Ala
    1310                1315                1320

Ala Ala Ala Ala Ala Ala Ala Ala Ala Ala Ala Ala Ala Ala
    1325                1330                1335

Ala Ala Ala Ala Ala Ala Ala Ala Ala Ala Ala Ala Ala Ala
    1340                1345                1350

Ala Ala Ala Ala Ala Ala Ala Ala Ala Ala Ala Ala Ala Ala
    1355                1360                1365

Ala Ala Ala Ala Ala Ala Ala Ala Ala Ala Ala Ala Ala Ala
    1370                1375                1380

Ala Ala Ala Ala Ala Ala Ala Ala Ala Ala Ala Ala Ala Gly
    1385                1390                1395

Gly Ala Asp Gly Gly Ala Ala Ala Ala Ala Ala Ala Ala Ala
    1400                1405                1410

Ala Ala Ala Ala Ala Ala Ala Ala Ala Ala Ala Ala Ala Ala
    1415                1420                1425

Ala Ala Ala Ala Ala Ala Ala Ala Ala Ala Ala Ala Ala Ala
    1430                1435                1440

Ala Ala Ala Ala Ala Ala Ala Ala Ala Ala Ala Ala Ala Ala
    1445                1450                1455

Ala Ala Ala Ala Ala Ala Ala Ala Ala Ala Ala Ala Ala Ala
    1460                1465                1470

Ala Ala Ala Ala Ala Ala Ala Ala Ala Ala Ala Ala Ala Ala

```
            1475                1480                1485

Ala Ala Ala Ala Ala Ala Ala  Ala Ala Ala Ala Ala  Ala Ala Ala
    1490                1495                1500

Ala Ala Ala Ala Ala Ala Ala  Ala Ala Ala Ala Ala  Ala Ala Ala
    1505                1510                1515

Ala Ala Ala Ala Ala Ala Ala  Ala Ala Ala Ala Ala  Ala Ala Ala
    1520                1525                1530

Ala Ala Ala Ala Ala Ala Ala  Ala Ala Ala Ala Ala  Ala Ala Ala
    1535                1540                1545

Ala Ala Ala Ala Ala Ala Ala  Ala Ala Ala Ala Ala  Ala Ala Ala
    1550                1555                1560

Ala Ala Ala Ala Ala Ala Ala  Ala Ala Ala Ala Ala  Ala Ala Ala
    1565                1570                1575

Ala Ala Ala Ala Ala Ala Ala  Ala Ala Ala Ala Ala  Ala Ala Ala
    1580                1585                1590

Ala Ala Ala Ala Gly Gly Ala  Asp Gly Gly Ala Ala  Ala Ala Ala
    1595                1600                1605

Ala Ala Ala Ala Ala Ala Ala  Ala Ala Ala Ala Ala  Ala Ala Ala
    1610                1615                1620

Ala Ala Ala Ala Ala Ala Ala  Ala Ala Ala Ala Ala  Ala Ala Ala
    1625                1630                1635

Ala Ala Ala Ala Ala Ala Ala  Ala Ala Ala Ala Ala  Ala Ala Ala
    1640                1645                1650

Ala Ala Ala Ala Ala Ala Ala  Ala Ala Ala Ala Ala  Ala Ala Ala
    1655                1660                1665

Ala Ala Ala Ala Ala Ala Ala  Ala Ala Ala Ala Ala  Ala Ala Ala
    1670                1675                1680

Ala Ala Ala Ala Ala Ala Ala  Ala Ala Ala Ala Ala  Ala Ala Ala
    1685                1690                1695

Ala Ala Ala Ala Ala Ala Ala  Ala Ala Ala Ala Ala  Ala Ala Ala
    1700                1705                1710

Ala Ala Ala Ala Ala Ala Ala  Ala Ala Ala Ala Ala  Ala Ala Ala
    1715                1720                1725

Ala Ala Ala Ala Ala Ala Ala  Ala Ala Ala Ala Ala  Ala Ala Ala
    1730                1735                1740

Ala Ala Ala Ala Ala Ala Ala  Ala Ala Ala Ala Ala  Ala Ala Ala
    1745                1750                1755

Ala Ala Ala Ala Ala Ala Ala  Ala Ala Ala Ala Ala  Ala Ala Ala
    1760                1765                1770

Ala Ala Ala Ala Ala Ala Ala  Ala Ala Ala Ala Ala  Ala Ala Ala
    1775                1780                1785

Ala Ala Ala Ala Ala Ala Ala  Ala Ala Gly Gly Ala  Asp Gly Gly
    1790                1795                1800

Ala Ala Ala Ala Ala Ala Ala  Ala Ala Ala Ala Ala  Ala Ala Ala
    1805                1810                1815

Ala Ala Ala Ala Ala Ala Ala  Ala Ala Ala Ala Ala  Ala Ala Ala
    1820                1825                1830

Ala Ala Ala Ala Ala Ala Ala  Ala Ala Ala Ala Ala  Ala Ala Ala
    1835                1840                1845

Ala Ala Ala Ala Ala Ala Ala  Ala Ala Ala Ala Ala  Ala Ala Ala
    1850                1855                1860

Ala Ala Ala Ala Ala Ala Ala  Ala Ala Ala Ala Ala  Ala Ala Ala
    1865                1870                1875
```

-continued

```
Ala Ala Ala Ala Ala Ala Ala  Ala Ala Ala Ala  Ala Ala Ala
    1880            1885             1890

Ala Ala Ala Ala Ala Ala Ala  Ala Ala Ala Ala  Ala Ala Ala
    1895            1900             1905

Ala Ala Ala Ala Ala Ala Ala  Ala Ala Ala Ala  Ala Ala Ala
    1910            1915             1920

Ala Ala Ala Ala Ala Ala Ala  Ala Ala Ala Ala  Ala Ala Ala
    1925            1930             1935

Ala Ala Ala Ala Ala Ala Ala  Ala Ala Ala Ala  Ala Ala Ala
    1940            1945             1950

Ala Ala Ala Ala Ala Ala Ala  Ala Ala Ala Ala  Ala Ala Ala
    1955            1960             1965

Ala Ala Ala Ala Ala Ala Ala  Ala Ala Ala Ala  Ala Ala Ala
    1970            1975             1980

Ala Ala Ala Ala Ala Ala Ala  Ala Ala Ala Ala  Ala Ala Gly
    1985            1990             1995

Gly Ala Asp Gly Gly Ala Ala  Ala Ala Ala Ala  Ala Ala Ala
    2000            2005             2010

Ala Ala Ala Ala Ala Ala Ala  Ala Ala Ala Ala  Ala Ala Ala
    2015            2020             2025

Ala Ala Ala Ala Ala Ala Ala  Ala Ala Ala Ala  Ala Ala Ala
    2030            2035             2040

Ala Ala Ala Ala Ala Ala Ala  Ala Ala Ala Ala  Ala Ala Ala
    2045            2050             2055

Ala Ala Ala Ala Ala Ala Ala  Ala Ala Ala Ala  Ala Ala Ala
    2060            2065             2070

Ala Ala Ala Ala Ala Ala Ala  Ala Ala Ala Ala  Ala Ala Ala
    2075            2080             2085

Ala Ala Ala Ala Ala Ala Ala  Ala Ala Ala Ala  Ala Ala Ala
    2090            2095             2100

Ala Ala Ala Ala Ala Ala Ala  Ala Ala Ala Ala  Ala Ala Ala
    2105            2110             2115

Ala Ala Ala Ala Ala Ala Ala  Ala Ala Ala Ala  Ala Ala Ala
    2120            2125             2130

Ala Ala Ala Ala Ala Ala Ala  Ala Ala Ala Ala  Ala Ala Ala
    2135            2140             2145

Ala Ala Ala Ala Ala Ala Ala  Ala Ala Ala Ala  Ala Ala Ala
    2150            2155             2160

Ala Ala Ala Ala Ala Ala Ala  Ala Ala Ala Ala  Ala Ala Ala
    2165            2170             2175

Ala Ala Ala Ala Ala Ala Ala  Ala Ala Ala Ala  Ala Ala Ala
    2180            2185             2190

Ala Ala Ala Ala Gly Gly Ala  Asp Gly Gly Ala  Ala Ala Ala
    2195            2200             2205

Ala Ala Ala Ala Ala Ala Ala  Ala Ala Ala Ala  Ala Ala Ala
    2210            2215             2220

Ala Ala Ala Ala Ala Ala Ala  Ala Ala Ala Ala  Ala Ala Ala
    2225            2230             2235

Ala Ala Ala Ala Ala Ala Ala  Ala Ala Ala Ala  Ala Ala Ala
    2240            2245             2250

Ala Ala Ala Ala Ala Ala Ala  Ala Ala Ala Ala  Ala Ala Ala
    2255            2260             2265

Ala Ala Ala Ala Ala Ala Ala  Ala Ala Ala Ala  Ala Ala Ala
    2270            2275             2280
```

-continued

Ala Ala Ala Ala Ala Ala Ala  Ala Ala Ala Ala  Ala Ala Ala
    2285            2290             2295

Ala Ala Ala Ala Ala Ala Ala  Ala Ala Ala Ala  Ala Ala Ala
    2300            2305             2310

Ala Ala Ala Ala Ala Ala Ala  Ala Ala Ala Ala  Ala Ala Ala
    2315            2320             2325

Ala Ala Ala Ala Ala Ala Ala  Ala Ala Ala Ala  Ala Ala Ala
    2330            2335             2340

Ala Ala Ala Ala Ala Ala Ala  Ala Ala Ala Ala  Ala Ala Ala
    2345            2350             2355

Ala Ala Ala Ala Ala Ala Ala  Ala Ala Ala Ala  Ala Ala Ala
    2360            2365             2370

Ala Ala Ala Ala Ala Ala Ala  Ala Ala Ala Ala  Ala Ala Ala
    2375            2380             2385

Ala Ala Ala Ala Ala Ala Ala  Ala Ala Gly Gly Ala  Asp Gly Gly
    2390            2395             2400

Ala Ala Ala Ala Ala Ala Ala  Ala Ala Ala Ala  Ala Ala Ala
    2405            2410             2415

Ala Ala Ala Ala Ala Ala Ala  Ala Ala Ala Ala  Ala Ala Ala
    2420            2425             2430

Ala Ala Ala Ala Ala Ala Ala  Ala Ala Ala Ala  Ala Ala Ala
    2435            2440             2445

Ala Ala Ala Ala Ala Ala Ala  Ala Ala Ala Ala  Ala Ala Ala
    2450            2455             2460

Ala Ala Ala Ala Ala Ala Ala  Ala Ala Ala Ala  Ala Ala Ala
    2465            2470             2475

Ala Ala Ala Ala Ala Ala Ala  Ala Ala Ala Ala  Ala Ala Ala
    2480            2485             2490

Ala Ala Ala Ala Ala Ala Ala  Ala Ala Ala Ala  Ala Ala Ala
    2495            2500             2505

Ala Ala Ala Ala Ala Ala Ala  Ala Ala Ala Ala  Ala Ala Ala
    2510            2515             2520

Ala Ala Ala Ala Ala Ala Ala  Ala Ala Ala Ala  Ala Ala Ala
    2525            2530             2535

Ala Ala Ala Ala Ala Ala Ala  Ala Ala Ala Ala  Ala Ala Ala
    2540            2545             2550

Ala Ala Ala Ala Ala Ala Ala  Ala Ala Ala Ala  Ala Ala Ala
    2555            2560             2565

Ala Ala Ala Ala Ala Ala Ala  Ala Ala Ala Ala  Ala Ala Ala
    2570            2575             2580

Ala Ala Ala Ala Ala Ala Ala  Ala Ala Ala Ala  Ala Ala Gly
    2585            2590             2595

Gly Ala Asp Gly Gly Ala Ala  Ala Ala Ala Ala  Ala Ala Ala
    2600            2605             2610

Ala Ala Ala Ala Ala Ala Ala  Ala Ala Ala Ala  Ala Ala Ala
    2615            2620             2625

Ala Ala Ala Ala Ala Ala Ala  Ala Ala Ala Ala  Ala Ala Ala
    2630            2635             2640

Ala Ala Ala Ala Ala Ala Ala  Ala Ala Ala Ala  Ala Ala Ala
    2645            2650             2655

Ala Ala Ala Ala Ala Ala Ala  Ala Ala Ala Ala  Ala Ala Ala
    2660            2665             2670

Ala Ala  Ala Ala Ala Ala Ala  Ala Ala Ala Ala Ala  Ala Ala Ala

-continued

| | | | |
|---|---|---|---|
| | 2675 | 2680 | 2685 |
| Ala Ala | Ala Ala Ala Ala Ala | Ala Ala Ala Ala Ala | Ala Ala Ala |
| 2690 | | 2695 | 2700 |
| Ala Ala | Ala Ala Ala Ala Ala | Ala Ala Ala Ala Ala | Ala Ala Ala |
| 2705 | | 2710 | 2715 |
| Ala Ala | Ala Ala Ala Ala Ala | Ala Ala Ala Ala Ala | Ala Ala Ala |
| 2720 | | 2725 | 2730 |
| Ala Ala | Ala Ala Ala Ala Ala | Ala Ala Ala Ala Ala | Ala Ala Ala |
| 2735 | | 2740 | 2745 |
| Ala Ala | Ala Ala Ala Ala Ala | Ala Ala Ala Ala Ala | Ala Ala Ala |
| 2750 | | 2755 | 2760 |
| Ala Ala | Ala Ala Ala Ala Ala | Ala Ala Ala Ala Ala | Ala Ala Ala |
| 2765 | | 2770 | 2775 |
| Ala Ala | Ala Ala Ala Ala Ala | Ala Ala Ala Ala Ala | Ala Ala Ala |
| 2780 | | 2785 | 2790 |
| Ala Ala | Ala Ala Gly Gly Ala | Asp Gly Gly Ala Ala | Ala Ala Ala |
| 2795 | | 2800 | 2805 |
| Ala Ala | Ala Ala Ala Ala Ala | Ala Ala Ala Ala Ala | Ala Ala Ala |
| 2810 | | 2815 | 2820 |
| Ala Ala | Ala Ala Ala Ala Ala | Ala Ala Ala Ala Ala | Ala Ala Ala |
| 2825 | | 2830 | 2835 |
| Ala Ala | Ala Ala Ala Ala Ala | Ala Ala Ala Ala Ala | Ala Ala Ala |
| 2840 | | 2845 | 2850 |
| Ala Ala | Ala Ala Ala Ala Ala | Ala Ala Ala Ala Ala | Ala Ala Ala |
| 2855 | | 2860 | 2865 |
| Ala Ala | Ala Ala Ala Ala Ala | Ala Ala Ala Ala Ala | Ala Ala Ala |
| 2870 | | 2875 | 2880 |
| Ala Ala | Ala Ala Ala Ala Ala | Ala Ala Ala Ala Ala | Ala Ala Ala |
| 2885 | | 2890 | 2895 |
| Ala Ala | Ala Ala Ala Ala Ala | Ala Ala Ala Ala Ala | Ala Ala Ala |
| 2900 | | 2905 | 2910 |
| Ala Ala | Ala Ala Ala Ala Ala | Ala Ala Ala Ala Ala | Ala Ala Ala |
| 2915 | | 2920 | 2925 |
| Ala Ala | Ala Ala Ala Ala Ala | Ala Ala Ala Ala Ala | Ala Ala Ala |
| 2930 | | 2935 | 2940 |
| Ala Ala | Ala Ala Ala Ala Ala | Ala Ala Ala Ala Ala | Ala Ala Ala |
| 2945 | | 2950 | 2955 |
| Ala Ala | Ala Ala Ala Ala Ala | Ala Ala Ala Ala Ala | Ala Ala Ala |
| 2960 | | 2965 | 2970 |
| Ala Ala | Ala Ala Ala Ala Ala | Ala Ala Ala Ala Ala | Ala Ala Ala |
| 2975 | | 2980 | 2985 |
| Ala Ala | Ala Ala Ala Ala Ala | Ala Ala Gly Gly Ala | Asp Gly Gly |
| 2990 | | 2995 | 3000 |
| Ala Ala | Ala Ala Ala Ala Ala | Ala Ala Ala Ala Ala | Ala Ala Ala |
| 3005 | | 3010 | 3015 |
| Ala Ala | Ala Ala Ala Ala Ala | Ala Ala Ala Ala Ala | Ala Ala Ala |
| 3020 | | 3025 | 3030 |
| Ala Ala | Ala Ala Ala Ala Ala | Ala Ala Ala Ala Ala | Ala Ala Ala |
| 3035 | | 3040 | 3045 |
| Ala Ala | Ala Ala Ala Ala Ala | Ala Ala Ala Ala Ala | Ala Ala Ala |
| 3050 | | 3055 | 3060 |
| Ala Ala | Ala Ala Ala Ala Ala | Ala Ala Ala Ala Ala | Ala Ala Ala |
| 3065 | | 3070 | 3075 |

-continued

```
Ala Ala Ala Ala Ala Ala Ala  Ala Ala Ala Ala  Ala Ala Ala
    3080            3085              3090

Ala Ala Ala Ala Ala Ala Ala  Ala Ala Ala Ala  Ala Ala Ala
    3095            3100              3105

Ala Ala Ala Ala Ala Ala Ala  Ala Ala Ala Ala  Ala Ala Ala
    3110            3115              3120

Ala Ala Ala Ala Ala Ala Ala  Ala Ala Ala Ala  Ala Ala Ala
    3125            3130              3135

Ala Ala Ala Ala Ala Ala Ala  Ala Ala Ala Ala  Ala Ala Ala
    3140            3145              3150

Ala Ala Ala Ala Ala Ala Ala  Ala Ala Ala Ala  Ala Ala Ala
    3155            3160              3165

Ala Ala Ala Ala Ala Ala Ala  Ala Ala Ala Ala  Ala Ala Ala
    3170            3175              3180

Ala Ala Ala Ala Ala Ala Ala  Ala Ala Ala Ala  Ala Ala Gly
    3185            3190              3195

Gly Ala Asp Gly Gly Ala Ala  Ala Ala Ala Ala  Ala Ala Ala
    3200            3205              3210

Ala Ala Ala Ala Ala Ala Ala  Ala Ala Ala Ala  Ala Ala Ala
    3215            3220              3225

Ala Ala Ala Ala Ala Ala Ala  Ala Ala Ala Ala  Ala Ala Ala
    3230            3235              3240

Ala Ala Ala Ala Ala Ala Ala  Ala Ala Ala Ala  Ala Ala Ala
    3245            3250              3255

Ala Ala Ala Ala Ala Ala Ala  Ala Ala Ala Ala  Ala Ala Ala
    3260            3265              3270

Ala Ala Ala Ala Ala Ala Ala  Ala Ala Ala Ala  Ala Ala Ala
    3275            3280              3285

Ala Ala Ala Ala Ala Ala Ala  Ala Ala Ala Ala  Ala Ala Ala
    3290            3295              3300

Ala Ala Ala Ala Ala Ala Ala  Ala Ala Ala Ala  Ala Ala Ala
    3305            3310              3315

Ala Ala Ala Ala Ala Ala Ala  Ala Ala Ala Ala  Ala Ala Ala
    3320            3325              3330

Ala Ala Ala Ala Ala Ala Ala  Ala Ala Ala Ala  Ala Ala Ala
    3335            3340              3345

Ala Ala Ala Ala Ala Ala Ala  Ala Ala Ala Ala  Ala Ala Ala
    3350            3355              3360

Ala Ala Ala Ala Ala Ala Ala  Ala Ala Ala Ala  Ala Ala Ala
    3365            3370              3375

Ala Ala Ala Ala Ala Ala Ala  Ala Ala Ala Ala  Ala Ala Ala
    3380            3385              3390

Ala Ala Ala Ala Gly Gly Ala  Asp Gly Gly Ala  Ala Ala Ala
    3395            3400              3405

Ala Ala Ala Ala Ala Ala Ala  Ala Ala Ala Ala  Ala Ala Ala
    3410            3415              3420

Ala Ala Ala Ala Ala Ala Ala  Ala Ala Ala Ala  Ala Ala Ala
    3425            3430              3435

Ala Ala Ala Ala Ala Ala Ala  Ala Ala Ala Ala  Ala Ala Ala
    3440            3445              3450

Ala Ala Ala Ala Ala Ala Ala  Ala Ala Ala Ala  Ala Ala Ala
    3455            3460              3465

Ala Ala Ala Ala Ala Ala Ala  Ala Ala Ala Ala  Ala Ala Ala
    3470            3475              3480
```

-continued

```
Ala Ala Ala Ala Ala Ala Ala  Ala Ala Ala Ala Ala  Ala Ala Ala
    3485              3490                  3495

Ala Ala Ala Ala Ala Ala Ala  Ala Ala Ala Ala Ala  Ala Ala Ala
    3500              3505                  3510

Ala Ala Ala Ala Ala Ala Ala  Ala Ala Ala Ala Ala  Ala Ala Ala
    3515              3520                  3525

Ala Ala Ala Ala Ala Ala Ala  Ala Ala Ala Ala Ala  Ala Ala Ala
    3530              3535                  3540

Ala Ala Ala Ala Ala Ala Ala  Ala Ala Ala Ala Ala  Ala Ala Ala
    3545              3550                  3555

Ala Ala Ala Ala Ala Ala Ala  Ala Ala Ala Ala Ala  Ala Ala Ala
    3560              3565                  3570

Ala Ala Ala Ala Ala Ala Ala  Ala Ala Ala Ala Ala  Ala Ala Ala
    3575              3580                  3585

Ala Ala Ala Ala Ala Ala Ala  Ala Ala Gly Gly Ala  Asp Gly Gly
    3590              3595                  3600

Ala Ala Ala Ala Ala Ala Ala  Ala Ala Ala Ala Ala  Ala Ala Ala
    3605              3610                  3615

Ala Ala Ala Ala Ala Ala Ala  Ala Ala Ala Ala Ala  Ala Ala Ala
    3620              3625                  3630

Ala Ala Ala Ala Ala Ala Ala  Ala Ala Ala Ala Ala  Ala Ala Ala
    3635              3640                  3645

Ala Ala Ala Ala Ala Ala Ala  Ala Ala Ala Ala Ala  Ala Ala Ala
    3650              3655                  3660

Ala Ala Ala Ala Ala Ala Ala  Ala Ala Ala Ala Ala  Ala Ala Ala
    3665              3670                  3675

Ala Ala Ala Ala Ala Ala Ala  Ala Ala Ala Ala Ala  Ala Ala Ala
    3680              3685                  3690

Ala Ala Ala Ala Ala Ala Ala  Ala Ala Ala Ala Ala  Ala Ala Ala
    3695              3700                  3705

Ala Ala Ala Ala Ala Ala Ala  Ala Ala Ala Ala Ala  Ala Ala Ala
    3710              3715                  3720

Ala Ala Ala Ala Ala Ala Ala  Ala Ala Ala Ala Ala  Ala Ala Ala
    3725              3730                  3735

Ala Ala Ala Ala Ala Ala Ala  Ala Ala Ala Ala Ala  Ala Ala Ala
    3740              3745                  3750

Ala Ala Ala Ala Ala Ala Ala  Ala Ala Ala Ala Ala  Ala Ala Ala
    3755              3760                  3765

Ala Ala Ala Ala Ala Ala Ala  Ala Ala Ala Ala Ala  Ala Ala Ala
    3770              3775                  3780

Ala Ala Ala Ala Ala Ala Ala  Ala Ala Ala Ala Ala  Ala Ala Gly
    3785              3790                  3795

Gly Ala Asp Gly Gly Ala Ala  Ala Ala Ala Ala Ala  Ala Ala Ala
    3800              3805                  3810

Ala Ala Ala Ala Ala Ala Ala  Ala Ala Ala Ala Ala  Ala Ala Ala
    3815              3820                  3825

Ala Ala Ala Ala Ala Ala Ala  Ala Ala Ala Ala Ala  Ala Ala Ala
    3830              3835                  3840

Ala Ala Ala Ala Ala Ala Ala  Ala Ala Ala Ala Ala  Ala Ala Ala
    3845              3850                  3855

Ala Ala Ala Ala Ala Ala Ala  Ala Ala Ala Ala Ala  Ala Ala Ala
    3860              3865                  3870

Ala Ala  Ala Ala Ala Ala Ala  Ala Ala Ala Ala Ala  Ala Ala Ala
```

-continued

```
                    3875                3880                3885

Ala Ala Ala Ala Ala Ala Ala Ala Ala Ala Ala Ala Ala Ala Ala
    3890                3895                3900

Ala Ala Ala Ala Ala Ala Ala Ala Ala Ala Ala Ala Ala Ala Ala
    3905                3910                3915

Ala Ala Ala Ala Ala Ala Ala Ala Ala Ala Ala Ala Ala Ala Ala
    3920                3925                3930

Ala Ala Ala Ala Ala Ala Ala Ala Ala Ala Ala Ala Ala Ala Ala
    3935                3940                3945

Ala Ala Ala Ala Ala Ala Ala Ala Ala Ala Ala Ala Ala Ala Ala
    3950                3955                3960

Ala Ala Ala Ala Ala Ala Ala Ala Ala Ala Ala Ala Ala Ala Ala
    3965                3970                3975

Ala Ala Ala Ala Ala Ala Ala Ala Ala Ala Ala Ala Ala Ala Ala
    3980                3985                3990

Ala Ala Ala Ala Gly Gly Ala Asp Gly Gly Ala Ala Ala Ala Ala
    3995                4000                4005

Ala Ala Ala Ala Ala Ala Ala Ala Ala Ala Ala Ala Ala Ala Ala
    4010                4015                4020

Ala Ala Ala Ala Ala Ala Ala Ala Ala Ala Ala Ala Ala Ala Ala
    4025                4030                4035

Ala Ala Ala Ala Ala Ala Ala Ala Ala Ala Ala Ala Ala Ala Ala
    4040                4045                4050

Ala Ala Ala Ala Ala Ala Ala Ala Ala Ala Ala Ala Ala Ala Ala
    4055                4060                4065

Ala Ala Ala Ala Ala Ala Ala Ala Ala Ala Ala Ala Ala Ala Ala
    4070                4075                4080

Ala Ala Ala Ala Ala Ala Ala Ala Ala Ala Ala Ala Ala Ala Ala
    4085                4090                4095

Ala Ala Ala Ala Ala Ala Ala Ala Ala Ala Ala Ala Ala Ala Ala
    4100                4105                4110

Ala Ala Ala Ala Ala Ala Ala Ala Ala Ala Ala Ala Ala Ala Ala
    4115                4120                4125

Ala Ala Ala Ala Ala Ala Ala Ala Ala Ala Ala Ala Ala Ala Ala
    4130                4135                4140

Ala Ala Ala Ala Ala Ala Ala Ala Ala Ala Ala Ala Ala Ala Ala
    4145                4150                4155

Ala Ala Ala Ala Ala Ala Ala Ala Ala Ala Ala Ala Ala Ala Ala
    4160                4165                4170

Ala Ala Ala Ala Ala Ala Ala Ala Ala Ala Ala Ala Ala Ala Ala
    4175                4180                4185

Ala Ala Ala Ala Ala Ala Ala Ala Gly Gly Ala Asp Gly Gly
    4190                4195                4200

Ala Ala Ala Ala Ala Ala Ala Ala Ala Ala Ala Ala Ala Ala Ala
    4205                4210                4215

Ala Ala Ala Ala Ala Ala Ala Ala Ala Ala Ala Ala Ala Ala Ala
    4220                4225                4230

Ala Ala Ala Ala Ala Ala Ala Ala Ala Ala Ala Ala Ala Ala Ala
    4235                4240                4245

Ala Ala Ala Ala Ala Ala Ala Ala Ala Ala Ala Ala Ala Ala Ala
    4250                4255                4260

Ala Ala Ala Ala Ala Ala Ala Ala Ala Ala Ala Ala Ala Ala Ala
    4265                4270                4275
```

-continued

```
Ala Ala Ala Ala Ala Ala  Ala Ala Ala Ala  Ala Ala Ala
    4280            4285              4290

Ala Ala Ala Ala Ala Ala  Ala Ala Ala Ala  Ala Ala Ala
    4295            4300              4305

Ala Ala Ala Ala Ala Ala  Ala Ala Ala Ala  Ala Ala Ala
    4310            4315              4320

Ala Ala Ala Ala Ala Ala  Ala Ala Ala Ala  Ala Ala Ala
    4325            4330              4335

Ala Ala Ala Ala Ala Ala  Ala Ala Ala Ala  Ala Ala Ala
    4340            4345              4350

Ala Ala Ala Ala Ala Ala  Ala Ala Ala Ala  Ala Ala Ala
    4355            4360              4365

Ala Ala Ala Ala Ala Ala  Ala Ala Ala Ala  Ala Ala Ala
    4370            4375              4380

Ala Ala Ala Ala Ala Ala  Ala Ala Ala Ala  Ala Ala Gly
    4385            4390              4395

Gly Ala Asp Gly Gly Ala  Ala Ala Ala Ala  Ala Ala Ala
    4400            4405              4410

Ala Ala Ala Ala Ala Ala  Ala Ala Ala Ala  Ala Ala Ala
    4415            4420              4425

Ala Ala Ala Ala Ala Ala  Ala Ala Ala Ala  Ala Ala Ala
    4430            4435              4440

Ala Ala Ala Ala Ala Ala  Ala Ala Ala Ala  Ala Ala Ala
    4445            4450              4455

Ala Ala Ala Ala Ala Ala  Ala Ala Ala Ala  Ala Ala Ala
    4460            4465              4470

Ala Ala Ala Ala Ala Ala  Ala Ala Ala Ala  Ala Ala Ala
    4475            4480              4485

Ala Ala Ala Ala Ala Ala  Ala Ala Ala Ala  Ala Ala Ala
    4490            4495              4500

Ala Ala Ala Ala Ala Ala  Ala Ala Ala Ala  Ala Ala Ala
    4505            4510              4515

Ala Ala Ala Ala Ala Ala  Ala Ala Ala Ala  Ala Ala Ala
    4520            4525              4530

Ala Ala Ala Ala Ala Ala  Ala Ala Ala Ala  Ala Ala Ala
    4535            4540              4545

Ala Ala Ala Ala Ala Ala  Ala Ala Ala Ala  Ala Ala Ala
    4550            4555              4560

Ala Ala Ala Ala Ala Ala  Ala Ala Ala Ala  Ala Ala Ala
    4565            4570              4575

Ala Ala Ala Ala Ala Ala  Ala Ala Ala Ala  Ala Ala Ala
    4580            4585              4590

Ala Ala Ala Ala Gly Gly  Ala Asp Gly Gly  Ala Ala Ala
    4595            4600              4605

Ala Ala Ala Ala Ala Ala  Ala Ala Ala Ala  Ala Ala Ala
    4610            4615              4620

Ala Ala Ala Ala Ala Ala  Ala Ala Ala Ala  Ala Ala Ala
    4625            4630              4635

Ala Ala Ala Ala Ala Ala  Ala Ala Ala Ala  Ala Ala Ala
    4640            4645              4650

Ala Ala Ala Ala Ala Ala  Ala Ala Ala Ala  Ala Ala Ala
    4655            4660              4665

Ala Ala Ala Ala Ala Ala  Ala Ala Ala Ala  Ala Ala Ala
    4670            4675              4680
```

Ala Ala Ala Ala Ala Ala Ala  Ala Ala Ala Ala Ala  Ala Ala Ala
        4685                4690                4695

Ala Ala Ala Ala Ala Ala Ala  Ala Ala Ala Ala Ala  Ala Ala Ala
        4700                4705                4710

Ala Ala Ala Ala Ala Ala Ala  Ala Ala Ala Ala Ala  Ala Ala Ala
        4715                4720                4725

Ala Ala Ala Ala Ala Ala Ala  Ala Ala Ala Ala Ala  Ala Ala Ala
        4730                4735                4740

Ala Ala Ala Ala Ala Ala Ala  Ala Ala Ala Ala Ala  Ala Ala Ala
        4745                4750                4755

Ala Ala Ala Ala Ala Ala Ala  Ala Ala Ala Ala Ala  Ala Ala Ala
        4760                4765                4770

Ala Ala Ala Ala Ala Ala Ala  Ala Ala Ala Ala Ala  Ala Ala Ala
        4775                4780                4785

Ala Ala Ala Ala Ala Ala Ala  Ala Ala Gly Gly Ala  Asp Gly Gly
        4790                4795                4800

Ala Ala Ala Ala Ala Ala Ala  Ala Ala Ala Ala Ala  Ala Ala Ala
        4805                4810                4815

Ala Ala Ala Ala Ala Ala Ala  Ala Ala Ala Ala Ala  Ala Ala Ala
        4820                4825                4830

Ala Ala Ala Ala Ala Ala Ala  Ala Ala Ala Ala Ala  Ala Ala Ala
        4835                4840                4845

Ala Ala Ala Ala Ala Ala Ala  Ala Ala Ala Ala Ala  Ala Ala Ala
        4850                4855                4860

Ala Ala Ala Ala Ala Ala Ala  Ala Ala Ala Ala Ala  Ala Ala Ala
        4865                4870                4875

Ala Ala Ala Ala Ala Ala Ala  Ala Ala Ala Ala Ala  Ala Ala Ala
        4880                4885                4890

Ala Ala Ala Ala Ala Ala Ala  Ala Ala Ala Ala Ala  Ala Ala Ala
        4895                4900                4905

Ala Ala Ala Ala Ala Ala Ala  Ala Ala Ala Ala Ala  Ala Ala Ala
        4910                4915                4920

Ala Ala Ala Ala Ala Ala Ala  Ala Ala Ala Ala Ala  Ala Ala Ala
        4925                4930                4935

Ala Ala Ala Ala Ala Ala Ala  Ala Ala Ala Ala Ala  Ala Ala Ala
        4940                4945                4950

Ala Ala Ala Ala Ala Ala Ala  Ala Ala Ala Ala Ala  Ala Ala Ala
        4955                4960                4965

Ala Ala Ala Ala Ala Ala Ala  Ala Ala Ala Ala Ala  Ala Ala Ala
        4970                4975                4980

Ala Ala Ala Ala Ala Ala Ala  Ala Ala Ala Ala Ala  Ala Ala Gly
        4985                4990                4995

Gly Ala Asp Gly Gly Ala Ala  Ala Ala Ala Ala Ala  Ala Ala Ala
        5000                5005                5010

Ala Ala Ala Ala Ala Ala Ala  Ala Ala Ala Ala Ala  Ala Ala Ala
        5015                5020                5025

Ala Ala Ala Ala Ala Ala Ala  Ala Ala Ala Ala Ala  Ala Ala Ala
        5030                5035                5040

Ala Ala Ala Ala Ala Ala Ala  Ala Ala Ala Ala Ala  Ala Ala Ala
        5045                5050                5055

Ala Ala Ala Ala Ala Ala Ala  Ala Ala Ala Ala Ala  Ala Ala Ala
        5060                5065                5070

Ala Ala Ala Ala Ala Ala Ala  Ala Ala Ala Ala Ala  Ala Ala Ala

-continued

```
            5075            5080            5085
Ala Ala  Ala Ala Ala Ala Ala  Ala Ala Ala Ala  Ala Ala Ala
5090            5095            5100
Ala Ala  Ala Ala Ala Ala Ala  Ala Ala Ala Ala  Ala Ala Ala
5105            5110            5115
Ala Ala  Ala Ala Ala Ala Ala  Ala Ala Ala Ala  Ala Ala Ala
5120            5125            5130
Ala Ala  Ala Ala Ala Ala Ala  Ala Ala Ala Ala  Ala Ala Ala
5135            5140            5145
Ala Ala  Ala Ala Ala Ala Ala  Ala Ala Ala Ala  Ala Ala Ala
5150            5155            5160
Ala Ala  Ala Ala Ala Ala Ala  Ala Ala Ala Ala  Ala Ala Ala
5165            5170            5175
Ala Ala  Ala Ala Ala Ala Ala  Ala Ala Ala Ala  Ala Ala Ala
5180            5185            5190
Ala Ala  Ala Ala Gly Gly Ala  Asp Gly Gly Ala  Ala Ala Ala
5195            5200            5205
Ala Ala  Ala Ala Ala Ala Ala  Ala Ala Ala Ala  Ala Ala Ala
5210            5215            5220
Ala Ala  Ala Ala Ala Ala Ala  Ala Ala Ala Ala  Ala Ala Ala
5225            5230            5235
Ala Ala  Ala Ala Ala Ala Ala  Ala Ala Ala Ala  Ala Ala Ala
5240            5245            5250
Ala Ala  Ala Ala Ala Ala Ala  Ala Ala Ala Ala  Ala Ala Ala
5255            5260            5265
Ala Ala  Ala Ala Ala Ala Ala  Ala Ala Ala Ala  Ala Ala Ala
5270            5275            5280
Ala Ala  Ala Ala Ala Ala Ala  Ala Ala Ala Ala  Ala Ala Ala
5285            5290            5295
Ala Ala  Ala Ala Ala Ala Ala  Ala Ala Ala Ala  Ala Ala Ala
5300            5305            5310
Ala Ala  Ala Ala Ala Ala Ala  Ala Ala Ala Ala  Ala Ala Ala
5315            5320            5325
Ala Ala  Ala Ala Ala Ala Ala  Ala Ala Ala Ala  Ala Ala Ala
5330            5335            5340
Ala Ala  Ala Ala Ala Ala Ala  Ala Ala Ala Ala  Ala Ala Ala
5345            5350            5355
Ala Ala  Ala Ala Ala Ala Ala  Ala Ala Ala Ala  Ala Ala Ala
5360            5365            5370
Ala Ala  Ala Ala Ala Ala Ala  Ala Ala Ala Ala  Ala Ala Ala
5375            5380            5385
Ala Ala  Ala Ala Ala Ala Ala  Ala Ala Gly Gly  Ala Asp Gly Gly
5390            5395            5400
Ala Ala  Ala Ala Ala Ala Ala  Ala Ala Ala Ala  Ala Ala Ala
5405            5410            5415
Ala Ala  Ala Ala Ala Ala Ala  Ala Ala Ala Ala  Ala Ala Ala
5420            5425            5430
Ala Ala  Ala Ala Ala Ala Ala  Ala Ala Ala Ala  Ala Ala Ala
5435            5440            5445
Ala Ala  Ala Ala Ala Ala Ala  Ala Ala Ala Ala  Ala Ala Ala
5450            5455            5460
Ala Ala  Ala Ala Ala Ala Ala  Ala Ala Ala Ala  Ala Ala Ala
5465            5470            5475
```

```
Ala Ala  Ala Ala Ala Ala  Ala Ala Ala Ala  Ala Ala Ala
    5480             5485             5490

Ala Ala  Ala Ala Ala Ala  Ala Ala Ala Ala  Ala Ala Ala
    5495             5500             5505

Ala Ala  Ala Ala Ala Ala  Ala Ala Ala Ala  Ala Ala Ala
    5510             5515             5520

Ala Ala  Ala Ala Ala Ala  Ala Ala Ala Ala  Ala Ala Ala
    5525             5530             5535

Ala Ala  Ala Ala Ala Ala  Ala Ala Ala Ala  Ala Ala Ala
    5540             5545             5550

Ala Ala  Ala Ala Ala Ala  Ala Ala Ala Ala  Ala Ala Ala
    5555             5560             5565

Ala Ala  Ala Ala Ala Ala  Ala Ala Ala Ala  Ala Ala Ala
    5570             5575             5580

Ala Ala  Ala Ala Ala Ala  Ala Ala Ala Ala  Ala Ala Gly
    5585             5590             5595

Gly Ala
    5600

<210> SEQ ID NO 61
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 2-40 "Gly Val Pro
      Gly Val" repeating units

<400> SEQUENCE: 61

Gly Val Pro Gly Val Gly Val Pro Gly Val Gly Val Pro Gly Val Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
                85                  90                  95

Val Pro Gly Val Gly Val Pro Gly Val Gly Val Pro Gly Val Gly Val
            100                 105                 110

Pro Gly Val Gly Val Pro Gly Val Gly Val Pro Gly Val Gly Val Pro
        115                 120                 125

Gly Val Gly Val Pro Gly Val Gly Val Pro Gly Val Gly Val Pro Gly
    130                 135                 140

Val Gly Val Pro Gly Val Gly Val Pro Gly Val Gly Val Pro Gly Val
145                 150                 155                 160

Gly Val Pro Gly Val Gly Val Pro Gly Val Gly Val Pro Gly Val Gly
                165                 170                 175

Val Pro Gly Val Gly Val Pro Gly Val Gly Val Pro Gly Val Gly Val
            180                 185                 190

Pro Gly Val Gly Val Pro Gly Val
        195                 200
```

```
<210> SEQ ID NO 62
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 10-200 Gly
      residues

<400> SEQUENCE: 62

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
                20                  25                  30

Gly Gly Gly Gly Gly Gly Gly Gly Gly Gly Gly Gly Gly Gly Gly
            35                  40                  45

Gly Gly Gly Gly Gly Gly Gly Gly Gly Gly Gly Gly Gly Gly Gly
        50                  55                  60

Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly
130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly
            180                 185                 190

Gly Gly Gly Gly Gly Gly Gly Gly
        195                 200

<210> SEQ ID NO 63
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 10-200 Ala
      residues

<400> SEQUENCE: 63

Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala
                20                  25                  30

Ala Ala Ala Ala Ala Ala Ala Ala Ala Ala Ala Ala Ala Ala Ala
            35                  40                  45

Ala Ala Ala Ala Ala Ala Ala Ala Ala Ala Ala Ala Ala Ala Ala
        50                  55                  60

Ala Ala Ala Ala Ala Ala Ala Ala Ala Ala Ala Ala Ala Ala Ala
```

```
                65                  70                  75                  80
Ala Ala Ala Ala Ala Ala Ala Ala Ala Ala Ala Ala Ala Ala Ala Ala
                    85                  90                  95

Ala Ala Ala Ala Ala Ala Ala Ala Ala Ala Ala Ala Ala Ala Ala Ala
            100                 105                 110

Ala Ala Ala Ala Ala Ala Ala Ala Ala Ala Ala Ala Ala Ala Ala Ala
        115                 120                 125

Ala Ala Ala Ala Ala Ala Ala Ala Ala Ala Ala Ala Ala Ala Ala Ala
        130                 135                 140

Ala Ala Ala Ala Ala Ala Ala Ala Ala Ala Ala Ala Ala Ala Ala Ala
145                 150                 155                 160

Ala Ala Ala Ala Ala Ala Ala Ala Ala Ala Ala Ala Ala Ala Ala Ala
            165                 170                 175

Ala Ala Ala Ala Ala Ala Ala Ala Ala Ala Ala Ala Ala Ala Ala Ala
        180                 185                 190

Ala Ala Ala Ala Ala Ala Ala Ala
        195                 200

<210> SEQ ID NO 64
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 3-66 "Gly Gly Ala"
      repeating units

<400> SEQUENCE: 64

Gly Gly Ala Gly Gly Ala Gly Gly Ala Gly Gly Ala Gly Gly Ala Gly
1               5                   10                  15

Gly Ala Gly Gly Ala Gly Gly Ala Gly Gly Ala Gly Gly Ala Gly Gly
            20                  25                  30

Ala Gly Gly Ala Gly Gly Ala Gly Gly Ala Gly Gly Ala Gly Gly Ala
        35                  40                  45

Gly Gly Ala Gly Gly Ala Gly Gly Ala Gly Gly Ala Gly Gly Ala Gly
    50                  55                  60

Gly Ala Gly Gly Ala Gly Gly Ala Gly Gly Ala Gly Gly Ala Gly Gly
65                  70                  75                  80

Ala Gly Gly Ala Gly Gly Ala Gly Gly Ala Gly Gly Ala Gly Gly Ala
            85                  90                  95

Gly Gly Ala Gly Gly Ala Gly Gly Ala Gly Gly Ala Gly Gly Ala Gly
            100                 105                 110

Gly Ala Gly Gly Ala Gly Gly Ala Gly Gly Ala Gly Gly Ala Gly Gly
        115                 120                 125

Ala Gly Gly Ala Gly Gly Ala Gly Gly Ala Gly Gly Ala Gly Gly Ala
        130                 135                 140

Gly Gly Ala Gly Gly Ala Gly Gly Ala Gly Gly Ala Gly Gly Ala Gly
145                 150                 155                 160

Gly Ala Gly Gly Ala Gly Gly Ala Gly Gly Ala Gly Gly Ala Gly Gly
            165                 170                 175

Ala Gly Gly Ala Gly Gly Ala Gly Gly Ala Gly Gly Ala Gly Gly Ala
        180                 185                 190

Gly Gly Ala Gly Gly Ala
        195
```

```
<210> SEQ ID NO 65
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 2-40 "Gly Val Gly
      Val Pro" repeating units

<400> SEQUENCE: 65

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
                20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
        50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
                100                 105                 110

Gly Val Pro Gly Val Gly Val Pro Gly Val Gly Val Pro Gly Val Gly
            115                 120                 125

Val Pro Gly Val Gly Val Pro Gly Val Gly Val Pro Gly Val Gly Val
        130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

Val Gly Val Pro Gly Val Gly Val Pro Gly Val Gly Val Pro Gly Val
                180                 185                 190

Gly Val Pro Gly Val Gly Val Pro
            195                 200

<210> SEQ ID NO 66
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 3-66 "Gly Pro Pro"
      repeating units

<400> SEQUENCE: 66

Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro Gly Pro
                20                  25                  30

Pro Gly Pro Pro Gly Pro Pro Gly Pro Pro Gly Pro Pro Gly Pro Pro
            35                  40                  45

Gly Pro Pro Gly Pro Pro Gly Pro Pro Gly Pro Pro Gly Pro Pro Gly
        50                  55                  60

Pro Pro Gly Pro Pro Gly Pro Pro Gly Pro Pro Gly Pro Pro Gly Pro
65                  70                  75                  80
```

```
Pro Gly Pro Pro Gly Pro Pro Gly Pro Pro Gly Pro Pro
                85                  90                  95

Gly Pro Pro Gly Pro Pro Gly Pro Pro Gly Pro Pro Gly
            100                 105                 110

Pro Pro Gly Pro Pro Gly Pro Pro Gly Pro Pro Gly Pro
        115                 120                 125

Pro Gly Pro Pro Gly Pro Pro Gly Pro Pro Gly Pro Pro
    130                 135                 140

Gly Pro Pro Gly Pro Pro Gly Pro Pro Gly Pro Pro Gly
145                 150                 155                 160

Pro Pro Gly Pro Pro Gly Pro Pro Gly Pro Pro Gly Pro
            165                 170                 175

Pro Gly Pro Pro Gly Pro Pro Gly Pro Pro Gly Pro Pro
        180                 185                 190

Gly Pro Pro Gly Pro Pro
        195

<210> SEQ ID NO 67
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 1-22 "Gly Ala Gln
      Gly Pro Ala Gly Pro Gly" repeating units

<400> SEQUENCE: 67

Gly Ala Gln Gly Pro Ala Gly Pro Gly Gly Ala Gln Gly Pro Ala Gly
1               5                   10                  15

Pro Gly Gly Ala Gln Gly Pro Ala Gly Pro Gly Gly Ala Gln Gly Pro
            20                  25                  30

Ala Gly Pro Gly Gly Ala Gln Gly Pro Ala Gly Pro Gly Gly Ala Gln
        35                  40                  45

Gly Pro Ala Gly Pro Gly Gly Ala Gln Gly Pro Ala Gly Pro Gly Gly
    50                  55                  60

Ala Gln Gly Pro Ala Gly Pro Gly Gly Ala Gln Gly Pro Ala Gly Pro
65                  70                  75                  80

Gly Gly Ala Gln Gly Pro Ala Gly Pro Gly Gly Ala Gln Gly Pro Ala
                85                  90                  95

Gly Pro Gly Gly Ala Gln Gly Pro Ala Gly Pro Gly Gly Ala Gln Gly
            100                 105                 110

Pro Ala Gly Pro Gly Gly Ala Gln Gly Pro Ala Gly Pro Gly Gly Ala
        115                 120                 125

Gln Gly Pro Ala Gly Pro Gly Gly Ala Gln Gly Pro Ala Gly Pro Gly
    130                 135                 140

Gly Ala Gln Gly Pro Ala Gly Pro Gly Gly Ala Gln Gly Pro Ala Gly
145                 150                 155                 160

Pro Gly Gly Ala Gln Gly Pro Ala Gly Pro Gly Gly Ala Gln Gly Pro
                165                 170                 175

Ala Gly Pro Gly Gly Ala Gln Gly Pro Ala Gly Pro Gly Gly Ala Gln
            180                 185                 190

Gly Pro Ala Gly Pro Gly
        195

<210> SEQ ID NO 68
```

```
<211> LENGTH: 195
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 1-13 "Gly Ala Pro
      Gly Ala Pro Gly Ser Gln Gly Ala Pro Gly Leu Gln" repeating units

<400> SEQUENCE: 68

Gly Ala Pro Gly Ala Pro Gly Ser Gln Gly Ala Pro Gly Leu Gln Gly
1               5                   10                  15

Ala Pro Gly Ala Pro Gly Ser Gln Gly Ala Pro Gly Leu Gln Gly Ala
                20                  25                  30

Pro Gly Ala Pro Gly Ser Gln Gly Ala Pro Gly Leu Gln Gly Ala Pro
            35                  40                  45

Gly Ala Pro Gly Ser Gln Gly Ala Pro Gly Leu Gln Gly Ala Pro Gly
        50                  55                  60

Ala Pro Gly Ser Gln Gly Ala Pro Gly Leu Gln Gly Ala Pro Gly Ala
65                  70                  75                  80

Pro Gly Ser Gln Gly Ala Pro Gly Leu Gln Gly Ala Pro Gly Ala Pro
                85                  90                  95

Gly Ser Gln Gly Ala Pro Gly Leu Gln Gly Ala Pro Gly Ala Pro Gly
                100                 105                 110

Ser Gln Gly Ala Pro Gly Leu Gln Gly Ala Pro Gly Ala Pro Gly Ser
            115                 120                 125

Gln Gly Ala Pro Gly Leu Gln Gly Ala Pro Gly Ala Pro Gly Ser Gln
        130                 135                 140

Gly Ala Pro Gly Leu Gln Gly Ala Pro Gly Ala Pro Gly Ser Gln Gly
145                 150                 155                 160

Ala Pro Gly Leu Gln Gly Ala Pro Gly Ala Pro Gly Ser Gln Gly Ala
                165                 170                 175

Pro Gly Leu Gln Gly Ala Pro Gly Ala Pro Gly Ser Gln Gly Ala Pro
            180                 185                 190

Gly Leu Gln
        195

<210> SEQ ID NO 69
<211> LENGTH: 195
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 1-13 "Gly Ala Pro
      Gly Thr Pro Gly Pro Gln Gly Leu Pro Gly Ser Pro" repeating units

<400> SEQUENCE: 69

Gly Ala Pro Gly Thr Pro Gly Pro Gln Gly Leu Pro Gly Ser Pro Gly
1               5                   10                  15

Ala Pro Gly Thr Pro Gly Pro Gln Gly Leu Pro Gly Ser Pro Gly Ala
                20                  25                  30

Pro Gly Thr Pro Gly Pro Gln Gly Leu Pro Gly Ser Pro Gly Ala Pro
            35                  40                  45

Gly Thr Pro Gly Pro Gln Gly Leu Pro Gly Ser Pro Gly Ala Pro Gly
        50                  55                  60

Thr Pro Gly Pro Gln Gly Leu Pro Gly Ser Pro Gly Ala Pro Gly Thr
65                  70                  75                  80
```

Pro Gly Pro Gln Gly Leu Pro Gly Ser Pro Gly Ala Pro Gly Thr Pro
            85                  90                  95

Gly Pro Gln Gly Leu Pro Gly Ser Pro Gly Ala Pro Gly Thr Pro Gly
        100                 105                 110

Pro Gln Gly Leu Pro Gly Ser Pro Gly Ala Pro Gly Thr Pro Gly Pro
        115                 120                 125

Gln Gly Leu Pro Gly Ser Pro Gly Ala Pro Gly Thr Pro Gly Pro Gln
        130                 135                 140

Gly Leu Pro Gly Ser Pro Gly Ala Pro Gly Thr Pro Gly Pro Gln Gly
145                 150                 155                 160

Leu Pro Gly Ser Pro Gly Ala Pro Gly Thr Pro Gly Pro Gln Gly Leu
                165                 170                 175

Pro Gly Ser Pro Gly Ala Pro Gly Thr Pro Gly Pro Gln Gly Leu Pro
            180                 185                 190

Gly Ser Pro
        195

<210> SEQ ID NO 70
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Gly Asp
1

<210> SEQ ID NO 71
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gly Val Pro Gly Val Gly Val Pro Gly Val Gly Gly Ala Gly Ala
1               5                   10                  15

Gly Ser Gly Ala Gly Ala Gly Ser Gly Ala Gly Ala Gly Ser
            20                  25                  30

<210> SEQ ID NO 72
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

His Ala Val
1

<210> SEQ ID NO 73
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

-continued

```
Leu Asp Val
1

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Ala Gly Ala Gly Ser Gly Ala Gly Ala Gly Ser Gly Ala Gly Ala
1               5                   10                  15

Gly Ser

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Gly Asp Ser
1
```